US007129078B2

(12) United States Patent
French et al.

(10) Patent No.: US 7,129,078 B2
(45) Date of Patent: *Oct. 31, 2006

(54) DNA ENCODING ANDROGEN RECEPTOR FRAGMENT

(75) Inventors: Frank S. French, Chapel Hill, NC (US); Elizabeth M. Wilson, Chapel Hill, NC (US); David R. Joseph, Chapel Hill, NC (US); Dennis Bryant Lubahn, Columbia, MO (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 102 days.

This patent is subject to a terminal disclaimer.

(21) Appl. No.: 10/886,384

(22) Filed: Jul. 7, 2004

(65) Prior Publication Data
US 2005/0079576 A1 Apr. 14, 2005

Related U.S. Application Data

(60) Continuation of application No. 09/497,822, filed on Feb. 3, 2000, now Pat. No. 6,821,767, which is a division of application No. 07/182,646, filed on Apr. 15, 1988, now Pat. No. 6,307,030.

(51) Int. Cl.
C12N 15/12 (2006.01)
C12N 5/10 (2006.01)

(52) U.S. Cl. .............. 435/232.3; 435/320.1; 435/325; 435/252.33; 435/172.3; 536/23.5

(58) Field of Classification Search ............ None
See application file for complete search history.

(56) References Cited

U.S. PATENT DOCUMENTS 4,423,208 A 12/1983 Grandics
5,614,620 A 3/1997 Liao et al.

FOREIGN PATENT DOCUMENTS

| EP | 0 365 657 B1 | 8/1999 |
| WO | WO 87/05049 | 8/1987 |
| WO | WO 89/09223 | 10/1989 |
| WO | WO 89/09791 A1 | 10/1989 |

OTHER PUBLICATIONS

Arriza et al.; *Cloning of Human Mineralocorticoid Receptor Complementary DNA: Structural and Functional Kinship with the Glucorticoid Receptor*, Science 237:268 (1987).
Barrack et al.; *A Critical Evaluation of the Use of Androgen Receptor Assays to Predict the Androgen Responsiveness of Prostatic Cancer*, Progress in Clinical and Biological Research, Coffey et al., Editors, 239:155 (1987).
Chang et al., *Molecular Cloning of Human and Rat Complementary DNA Encoding Androgen Receptors*, Science, 240:324-326 (1988).
Chang et al., *Structural analysis of complementary DNA and amino acid sequences of human and rat androgen receptors*, Proceedings of the National Academy of Sciences of the USA, 85:7211-7215 (1988).
Foekens et al., *Purification of the androgen receptor of sheep seminal vesicles*, Biochemical and Biophysical Research Communications, 104:1279-1286(1982).
Foekens, et al.; *Purification of the androgen receptor of sheep seminal vesicles*, Chemical Abstracts, 96:136059r; p. 106 (1982).
Govindan, *Cloning of the human androgen receptor of cDNA*, Chemical Absracts,109(23), p. 205 (1988).
Green, *Human oestrogen receptor cDNA. sequence, expression and homology to v-erb-A*, Nature, 320:134-139 (1986).
Greene et al.; *Sequence and Expression of Human Estrogen Receptor Complementary DNA*, Science 231:1150 (1986 ).
Hollenberg et al.; *Primary Structure and Expression of a Functional Human Glucocorticoid Receptor cDNA*, Science 318:635 (1986).
Johnson et al.; *A Common Molecular Weight of the Androgen Receptor Monomer in Different Target Tissues*, Biochemistry 26:3174-3182 (Jun. 2, 1987).
Lubahn et al., *The human androgen receptor: complementary deoxyribonucleic acid cloning, sequence analysis and gene expression in prostate*, Molecular Endocrinology, 2:1265-1275 (1988).
Lubahn, *Cloning of Human Androgen Receoptor Complementary DNA and Localization to the X Chromosome*; Science, 240:327-330 (1988).
Misrahi et al.; *Complete Amino Acid Sequence of the Human Progesterone Receptor Deduced from Cloned cDNA*, Biophys. Res. Comm. 143:740 (1987).
Murthy et al.; *Physicochemical Characterization of the Androgen Receptor From Hyperplastic Human Prostate*, The Prostate 5:567-579 (1984).
Rowley et al.; *Properties of an Intermediate-Sized Androgen Receptor: Association with RNA*, Biochemistry 25:6988-6995 (1986).
Tilley et al. *Characterization and expression of a cDNA encoding the human androgen receptor*, Proceedings of the National Academy of Sciences of the USA, 86:327-331 (1989).
Trapman, *Cloning Structure and Expression of a cDNA Encoding the Human Androgen Receptor*, Biochemical and Biophysical Research Communications, 153:241-248 (1988).
Weinberger, *The c-erb-A gene encodes a thyroid hormone receptor*, Nature, 324:641-646 (1986).

*Primary Examiner*—Michael Pak
(74) *Attorney, Agent, or Firm*—Myers Bigel Sibley & Sajovec, P.A.

(57) ABSTRACT

DNA sequences encoding human androgen receptor protein and polypeptides and proteins having substantially the same biological activity as human androgen receptor protein and the amino acid sequences of human androgen receptor protein and polypeptides and proteins having substantially the same biological activity as human androgen receptor protein are disclosed. Methods for the production and use of such compositions are also disclosed.

7 Claims, 23 Drawing Sheets

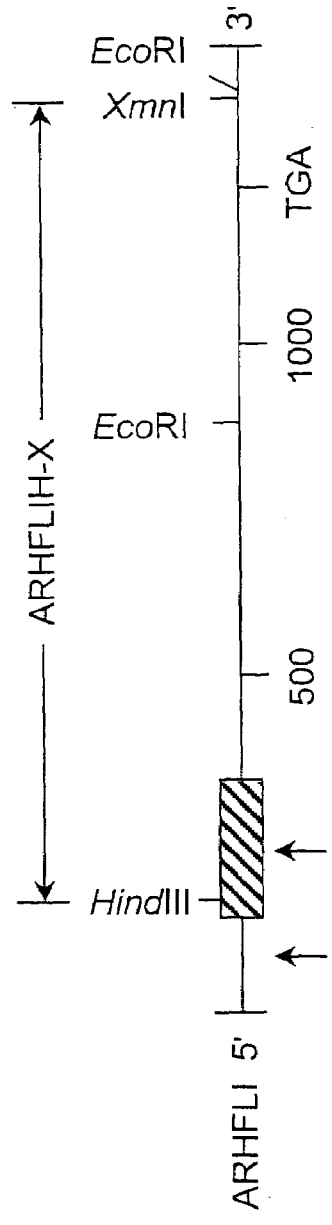

DNA-BINDING DOMAIN

```
                              +         +           10          +    20+          +           30
hAR    (SEQ ID NO:9)  (AA 567) K Q K Y L C L I I C G D E A S G C H Y G A L T C G S C K V F F K R A A E G (100%)
hPR    (SEQ ID NO:10) (AA 603) Q Q H N Y L C L I H C G D E A S G C H Y G V L T C G S C K V F F K R A M E G (94%)
hMR    (SEQ ID NO:11) (AA 421) Q H N Y L C L V C G D E A S G C H Y G V V T C G S C K V F F K R A V E G (87%)
hGR    (SEQ ID NO:12) (AA 185) Q H N Y L C L V C S D E A S G C H Y G V L T C G S C K V F F K R A V E G (87%)
hER    (SEQ ID NO:13)          H N D Y M C A V C N D Y A S G Y H Y G V W S C E G C K A F F K R S I Q G (55%)
cVDR   (SEQ ID NO:14)          K A M F T C G V C G D R A T G F H F N A M T C E G C K G F F R R S M K R (48%)
hT3R   (SEQ ID NO:15) (AA 102) N L H P S Y S C V V C G D K A T G Y H Y R C I T C E G C K G F F R R T I Q K (48%)
vERBA  (SEQ ID NO:16) (AA 37)  N L H P T T S C V V C G D K A T G Y H Y R C I T C E G C K S F F R R T I Q K (48%)
hRAR   (SEQ ID NO:17) (AA 58)  N M V Y T C F V C G D K S S G Y H Y G V S A C E G C K G F F R R S I Q K (45%)
```

```
                              +         +           40          +    50          +           60+
hAR    (SEQ ID NO:9)           K Q K Y L C A S R N D C T I D K F R R K N C P S C R L R K C Y E A G M (100%)
hPR    (SEQ ID NO:10)          Q H N Y L C A G R N D C I V D K I R R K N C P A C R L R K C C Q A G M (71%)
hMR    (SEQ ID NO:11)          Q H N Y L C A G R N D C I I D K I R R K N C P A C R Y R K C L Q A G M (71%)
hGR    (SEQ ID NO:12)          Q H N Y L C A G R N D C I I D K I R R K N C P A C R Y R K C L Q A G M (71%)
hER    (SEQ ID NO:13)          H N D Y M C P A T N Q C T I D K N R R K S C Q A C R L R K C Y E V G M (63%)
cVDR   (SEQ ID NO:14)          K A M F T C P F N G D C K I T K D N R R H C Q A C R L K R C V D I G M (40%)
hT3R   (SEQ ID NO:15)          H P S Y S C K Y E G K C V I D K V T R N Q C C Q L C R F K K C I Y V G M (40%)
vERBA  (SEQ ID NO:16)          H P T T S C T Y D G C C V I D K I T R N Q C Q L C R F K K C I S V G M (37%)
hRAR   (SEQ ID NO:17)          N M V Y T C H R D K N C I I N K V T R N R C Q Y C R L Q K C F E V G M (43%)
```

FIG. 1C

```
         10                    30                    50
          .                     .                     .
          .                     .                     .
GAGCTCTGGACAAAATTGAGCGCCTATGTGTACATGGCAAGTGTTTTTAGTGTTTGTGTG
CTCGAGACCTGTTTTAACTCGCGGATACACATGTACCGTTCACAAAAATCACAAACACAC 70                    90                   110
          .                     .                     .
          .                     .                     .
TTTACCTGCTTGTCTGGGTGATTTTGCCTTTGAGAGTCTGGATGAGAAATGCATGGTTAA
AAATGGACGAACAGACCCACTAAAACGGAAACTCTCAGACCTACTCTTTACGTACCAATT 130                   150                   170
          .                     .                     .
          .                     .                     .
AGGCAATTCCAGACAGGAAGAAAGGCAGAGAAGAGGGTAGAAATGACCTCTGATTCTTGG
TCCGTTAAGGTCTGTCCTTCTTTCCGTCTCTTCTCCCATCTTTACTGGAGACTAAGAACC 190                   210                   230
          .                     .                     .
          .                     .                     .
GGCTGAGGGTTCCTAGAGCAAATGGCACAATGCCACGAGGCCCGATCTATCCCTATGACG
CCGACTCCCAAGGATCTCGTTTACCGTGTTACGGTGCTCCGGGCTAGATAGGGATACTGC 250                   270                   290
          .                     .                     .
          .                     .                     .
GAACTCTAAGGTTTCAGCATCAGCTATCTGCTGGCTTGGTCACTGGCTTGCCTCCTCAGT
CTTGAGATTCCAAAGTCGTAGTCGATAGACGACCGAACCAGTGACCGAACGGAGGAGTCA 310                   330                   350
          .                     .                     .
          .                     .                     .
TTGTAGGAGACTCTCCCACTCTCCCATCTGCGCGCTCTTATCAGTCCTGAAAAGAACCCN
AACATCCTCTGAGAGGGTGAGAGGGTAGACGCGCGAGAATAGTCAGGACTTTTCTTGGGN 370                   390                   410
          .                     .                     .
          .                     .                     .
TGGCNAGCCAGGAGCNAGGTATTCNTATCGTCCTTTTCNTCCTCCTNGCCTCACCTNGTT
ACCGNTCGGTCCTCGNTCCATAAGNATAGCAGGAAAAGNAGGAGGANCGGAGTGGANCAA 430                   450                   470
          .                     .                     .
          .                     .                     .
GNTTTTTAGATTGGNCTTNGNAACCAAATTGTATGCTGGCCTCCAGGAAATCTGGAGCC
CNAAAAATCTAACCNGAANCNTTGGTTTAAACATACGACCGGAGGTCCTTTAGACCTCGG 490                   510                   530
          .                     .                     .
          .                     .                     .
TGGCGCCTAAACCTTGGTTTAGGAAAGCAGGAGCTATTCAGGAAGCAGGGTCCTCCAGGG
ACCGCGGATTTGGAACCAAATCCTTTCGTCCTCGATAAGTCCTTCGTCCCAGGAGGTCCC 550                   570                   590
          .                     .                     .
          .                     .                     .
CTAGAGCTAGCCTCTCCTGCCCTCGCCCACGTGCGCCAGCACTTGTTTCTCCAAAGCNAC
GATCTCGATCGGAGAGGACGGGAGCGGGTGCACGCGGTCGTGAACAAAGAGGTTTCGNTG
```

*FIG. 4A*

```
            610                  630                  650
             .                    .                    .
             .                    .                    .
TAGGCAGGCGTTAGCGCGCGGTGAGGGGAGGGGAGAAAAGGAAAGGGGAGGGGAGGGAAA
ATCCGTCCGCAATCGCGCGCCACTCCCCTCCCCTCTTTTCCTTTCCCCTCCCCTCCCTTT 670                  690                  710
             .                    .                    .
             .                    .                    .
AGGAGGTGGGAAGGCAAGGAGGCCGGCCNGGTGGGGGCGGGACCCGACTCGCANNAACTG
TCCTCCACCCTTCCGTTCCTCCGGCCGGNCCACCCCCGCCCTGGGCTGAGCGTNNTTGAC 730                  750                  770
             .                    .                    .
             .                    .                    .
TTGCATTTGCTCTCCACCTCCCAGCGCCCCTCCGAGATCCCGGGGAGCCAGCTTGCTGG
AACGTAAACGAGAGGTGGAGGGTCGCGGGGAGGCTCTAGGGCCCCTCGGTCGAACGACC 790                  810                  830
             .                    .                    .
             .                    .                    .
GAGAGCGGGAACGGTCCGGAGCAAGCCCAGAGGCAGAGGAGGCGACAGAGGGAAAAAGGG
CTCTCGCCCTTGCCAGGCCTCGTTCGGGTCTCCGTCTCCTCCGCTGTCTCCCTTTTCCC 850                  870                  890
             .                    .                    .
             .                    .                    .
CCCNAGCTAGCCGCTCCAGTGCTGTACAGNAGCCGAAGGACGCACCACGCCAGCCCCAGC
GGGNTCGATCGGCGAGGTCACGACATGTCNTCGGCTTCCTGCGTGGTGCGGTCGGGGTCG 910                  930                  950
             .                    .                    .
             .                    .                    .
CCGGCTCCAGCGACAGCNAACGCCTCTTGCANGCGTTCGAAGCCGCCGCCCGGAGCTGCC
GGCCGAGGTCGCTGTCGNTTGCGGAGAACGTNCGCAAGCTTCGGCGGCGGGCCTCGACGG 970                  990                 1010
             .                    .                    .
             .                    .                    .
CTTTCCTCTTCGGTGAAGTTTTTAAAAGCTGCTAAAGACTCGGAGGAAGCAAGGAAAGTG
GAAAGGAGAAGCCACTTCAAAAATTTTCGACGATTTCTGAGCCTCCTTCGTTCCTTTCAC 1030                 1050                 1070
             .                    .                    .
             .                    .                    .
CCTGGTAGGACTGACGGCTGCCTTTGTCCTCCTCCTCTCCACCCCGCCTCCCCCCACCCT
GGACCATCCTGACTGCCGACGGAAACAGGAGGAGGAGAGGTGGGGCGGAGGGGGGTGGGA 1090                 1110                 1130
             .                    .                    .
             .                    .                    .
GCCTTCCCCCCCTCCCCCGTCTTCTCTCCCGCAGCTGCCTCAGTCGGCTACTCTCAGCCA
CGGAAGGGGGGGAGGGGGCAGAAGAGAGGGCGTCGACGGAGTCAGCCGATGAGAGTCGGT 1150                 1170                 1190
             .                    .                    .
             .                    .                    .
ACCCCCCTCACCACCCTTCTCCCCACCCGCCCCCCGCCCCCGTCGGCCCAGCGNTGNCA
TGGGGGGAGTGGTGGGAAGAGGGGTGGGCGGGGGGCGGGGGCAGCCGGGTCGCNACNGT
```

*FIG. 4B*

```
         1210                1230                 1250
           .                   .                    .
    .       .        .       .       .       .       .
GNCCGAGTTTGCAGAGAGGTAACTCCCTTTGGCTGCGAGCGGGCGAGNCTAGCTGCACAT
CNGGCTCAAACGTCTCTCCATTGAGGGAAACCGACGCTCGCCCGCTCNGATCGACGTGTA 1270                1290                 1310
           .                   .                    .
    .       .        .       .       .       .       .
TGCAAAGAAGGCTCTTAGGAGCAGGCGACTGGGGAGCGGCTTCAGCACTGCAGCCACGAC
ACGTTTCTTCCGAGAATCCTCGTCCGCTGACCCCTCGCCGAAGTCGTGACGTCGGTGCTG 1330                1350                 1370
           .                   .                    .
    .       .        .       .       .       .       .
CNGCCTGGTTAGGCTGCACGCGGAGAGAACCCTCTGTTTTCCCCCACTCTCTCTCCACCT
GNCGGACCAATCCGACGTGCGCCTCTCTTGGGAGACAAAAGGGGGTGAGAGAGAGGTGGA 1390                1410                 1430
           .                   .                    .
    .       .        .       .       .       .       .
CCTCCTGCCTTCCCCACCCCGAGTGCGGAGCCAGAGATCAAAAGATGAAAAGGCAGTCAG
GGAGGACGGAAGGGGTGGGGCTCACGCCTCGGTCTCTAGTTTTCTACTTTTCCGTCAGTC 1450                1470                 1490
           .                   .                    .
    .       .        .       .       .       .       .
GTCTTCAGTAGCCAAAAAACAAAACAAACAAAAACAAAAAAGCCGAAATAAAAGAAAAAG
CAGAAGTCATCGGTTTTTTGTTTTGTTTGTTTTTGTTTTTTCGGCTTTATTTTCTTTTTC 1510                1530                 1550
           .                   .                    .
    .       .        .       .       .       .       .
ATAATAACTCAGTTCTTATTTGCACCTACTTCAGTGGACACTGAATTTGGAAGGTGGAGG
TATTATTGAGTCAAGAATAAACGTGGATGAAGTCACCTGTGACTTAAACCTTCCACCTCC 1570                1590                 1610
           .                   .                    .
    .       .        .       .       .       .       .
ATTTTGTTTTTTTCTTTTAAGATCTGGGCATCTTTTGAATCTACCCTTCAAGTATTAAGA
TAAAACAAAAAAAGAAAATTCTAGACCCGTAGAAAACTTAGATGGGAAGTTCATAATTCT 1630                1650                 1670
           .                   .                    .
    .       .        .       .       .       .       .
GACAGACTGTGAGCCTAGCAGGGCAGATCTTGTCCACCGTGTGTCTTCTTCTGCACGAGA
CTGTCTGACACTCGGATCGTCCCGTCTAGAACAGGTGGCACACAGAAGAAGACGTGCTCT 1690                1710                 1730
           .                   .                    .
    .       .        .       .       .       .       .
CTTTGAGGCTGTCAGAGCGCTTTTTGCGTGGTTGCTCCCGCAAGTTTCCTTCTCTGGAGC
GAAACTCCGACAGTCTCGCGAAAAACGCACCAACGAGGGCGTTCAAAGGAAGAGACCTCG 1750                1770                 1790
           .                   .                    .
    .       .        .       .       .       .       .
TTCCCGCAGGTGGGCAGCTAGCTGCAGCGACTACCGCATCATCACAGCCTGTTGAACTCT
AAGGGCGTCCACCCGTCGATCGACGTCGCTGATGGCGTAGTAGTGTCGGACAACTTGAGA
```

FIG. 4C

```
              1810                  1830                  1850
               .                     .                     .
           .         .           .         .          .         .
    TCTGAGCAAGAGAAGGGGAGGCGGGGTAAGGGAAGTAGGTGGAAGATTCAGCCAAGCTCA
    AGACTCGTTCTCTTCCCCTCCGCCCCATTCCCTTCATCCACCTTCTAAGTCGGTTCGAGT 1870                  1890                  1910
               .                     .                     .
           .         .           .         .          .         .
    AGGATGGAAGTGCAGTTAGGGCTGGGAAGGGTCTACCCTCGGCCGCCGTCCAAGACCTAC
    TCCTACCTTCACGTCAATCCCGACCCTTCCCAGATGGGAGCCGGCGGCAGGTTCTGGATG 1930                  1950                  1970
               .                     .                     .
           .         .           .         .          .         .
    CGAGGAGCTTTCCAGAATCTGTTCCAGAGCGTGCGCGAAGTGATCCAGAACCCGGGCCCC
    GCTCCTCGAAAGGTCTTAGACAAGGTCTCGCACGCGCTTCACTAGGTCTTGGGCCCGGGG 1990                  2010                  2030
               .                     .                     .
           .         .           .         .          .         .
    AGGCACCCAGAGGCCGCGAGCGCAGCACCTCCCGGCGCCAGTTTGCTGCTGCTGCAGCAG
    TCCGTGGGTCTCCGGCGCTCGCGTCGTGGAGGGCCGCGGTCAAACGACGACGACGTCGTC 2050                  2070                  2090
               .                     .                     .
           .         .           .         .          .         .
    CAGCAGCAGCAGCAGCAGCAGCAGCAGCAGCAGCAGCAGCAGCAGCAGCAGCAGCAGCAG
    GTCGTCGTCGTCGTCGTCGTCGTCGTCGTCGTCGTCGTCGTCGTCGTCGTCGTCGTCGTC 2110                  2130                  2150
               .                     .                     .
           .         .           .         .          .         .
    CAGCAGCAAGAGACTAGCCCCAGGCAGCAGCAGCAGCAGCAGGGTGAGGATGGTTCTCCC
    GTCGTCGTTCTCTGATCGGGGTCCGTCGTCGTCGTCGTCGTCCCACTCCTACCAAGAGGG 2170                  2190                  2210
               .                     .                     .
           .         .           .         .          .         .
    CAAGCCCATCGTAGAGGCCCCACAGGCTACCTGGTCCTGGATGAGGAACAGCAACCTTCA
    GTTCGGGTAGCATCTCCGGGGTGTCCGATGGACCAGGACCTACTCCTTGTCGTTGGAAGT 2230                  2250                  2270
               .                     .                     .
           .         .           .         .          .         .
    CAGCCGCAGTCGGCCCTGGAGTGCCACCCCGAGAGAGGTTGCGTCCCAGAGCCTGGAGCC
    GTCGGCGTCAGCCGGGACCTCACGGTGGGGCTCTCTCCAACGCAGGGTCTCGGACCTCGG 2290                  2310                  2330
               .                     .                     .
           .         .           .         .          .         .
    GCCGTGGCCGCCAGCAAGGGGCTGCCGCAGCAGCTGCCAGCACCTCCGGACGAGGATGAC
    CGGCACCGGCGGTCGTTCCCCGACGGCGTCGTCGACGGTCGTGGAGGCCTGCTCCTACTG 2350                  2370                  2390
               .                     .                     .
           .         .           .         .          .         .
    TCAGCTGCCCCATCCACGTTGTCCCTGCTGGGCCCCACTTTCCCCGGCTTAAGCAGCTGC
    AGTCGACGGGGTAGGTGCAACAGGGACGACCCGGGGTGAAAGGGGCCGAATTCGTCGACG
```

*FIG. 4D*

```
          2410              2430              2450
            .                 .                 .
TCCGCTGACCTTAAAGACATCCTGAGCGAGGCCAGCACCATGCAACTCCTTCAGCAACAG
AGGCGACTGGAATTTCTGTAGGACTCGCTCCGGTCGTGGTACGTTGAGGAAGTCGTTGTC 2470              2490              2510
            .                 .                 .
CAGCAGGAAGCAGTATCCGAAGGCAGCAGCAGCGGGAGAGCGAGGGAGGCCTCGGGGGCT
GTCGTCCTTCGTCATAGGCTTCCGTCGTCGTCGCCCTCTCGCTCCCTCCGGAGCCCCCGA 2530              2550              2570
            .                 .                 .
CCCACTTCCTCCAAGGACAATTACTTAGGGGGCACTTCGACCATTTCTGACAACGCCAAG
GGGTGAAGGAGGTTCCTGTTAATGAATCCCCCGTGAAGCTGGTAAAGACTGTTGCGGTTC 2590              2610              2630
            .                 .                 .
GAGTTGTGTAAGGCAGTGTCGGTGTCCATGGGCCTGGGTGTGGAGGCGTTGGAGCATCTG
CTCAACACATTCCGTCACAGCCACAGGTACCCGGACCCACACCTCCGCAACCTCGTAGAC 2650              2670              2690
            .                 .                 .
AGTCCAGGGGAACAGCTTCGGGGGGATTGCATGTACGCCCCACTTTTGGGAGTTCCACCC
TCAGGTCCCCTTGTCGAAGCCCCCCTAACGTACATGCGGGGTGAAAACCCTCAAGGTGGG 2710              2730              2750
            .                 .                 .
GCTGTGCGTCCCACTCCTTGTGCCCCATTGGCCGAATGCAAAGGTTCTCTGCTAGACGAC
CGACACGCAGGGTGAGGAACACGGGGTAACCGGCTTACGTTTCCAAGAGACGATCTGCTG 2770              2790              2810
            .                 .                 .
AGCGCAGGCAAGAGCACTGAAGATACTGCTGAGTATTCCCCTTTCAAGGGAGGTTACACC
TCGCGTCCGTTCTCGTGACTTCTATGACGACTCATAAGGGGAAAGTTCCCTCCAATGTGG 2830              2850              2870
            .                 .                 .
AAAGGGCTAGAAGGCGAGAGCCTAGGCTGCTCTGGCAGCGCTGCAGCAGGGAGCTCCGGG
TTTCCCGATCTTCCGCTCTCGGATCCGACGAGACCGTCGCGACGTCGTCCCTCGAGGCCC 2890              2910              2930
            .                 .                 .
ACACTTGAACTGCCGTCTACCCTGTCTCTCTACAAGTCCGGAGCACTGGACGAGGCAGCT
TGTGAACTTGACGGCAGATGGGACAGAGAGATGTTCAGGCCTCGTGACCTGCTCCGTCGA 2950              2970              2990
            .                 .                 .
GCGTACCAGAGTCGCGACTACTACAACTTTCCACTGGCTCTGGCCGGACCGCCGCCCCT
CGCATGGTCTCAGCGCTGATGATGTTGAAAGGTGACCGAGACCGGCCTGGCGGCGGGGA
```

FIG. 4E

```
              3010                  3030                  3050
               .                     .                     .
        CCGCCGCCTCCCCATCCCCACGCTCGCATCAAGCTGGAGAACCCGCTGGACTACGGCAGC
        GGCGGCGGAGGGGTAGGGGTGCGAGCGTAGTTCGACCTCTTGGGCGACCTGATGCCGTCG 3070                  3090                  3110
               .                     .                     .
        GCCTGGGCGGCTGCGGCGGCGCAGTGCCGCTATGGGGACCTGGCGAGCCTGCATGGCGCG
        CGGACCCGCCGACGCCGCCGCGTCACGGCGATACCCCTGGACCGCTCGGACGTACCGCGC 3130                  3150                  3170
               .                     .                     .
        GGTGCAGCGGGACCCGGTTCTGGGTCACCCTCAGCCGCCGCTTCCTCATCCTGGCACACT
        CCACGTCGCCCTGGGCCAAGACCCAGTGGGAGTCGGCGGCGAAGGAGTAGGACCGTGTGA 3190                  3210                  3230
               .                     .                     .
        CTCTTCACAGCCGAAGAAGGCCAGTTGTATGGACCGTGTGGTGGTGGTGGGGGTGGTGGC
        GAGAAGTGTCGGCTTCTTCCGGTCAACATACCTGGCACACCACCACCACCCCCACCACCG 3250                  3270                  3290
               .                     .                     .
        GGCGGCGGCGGCGGCGGCGGCGGCGGCGGCGGCGGCGGCGGCGGCGGCGGCGAGGCGGGA
        CCGCCGCCGCCGCCGCCGCCGCCGCCGCCGCCGCCGCCGCCGCCGCCGCCGCCGCTCCGCCCT 3310                  3330                  3350
               .                     .                     .
        GCTGTAGCCCCCTACGGCTACACTCGGCCCCCTCAGGGGCTGGCGGGCCAGGAAAGCGAC
        CGACATCGGGGGATGCCGATGTGAGCCGGGGGAGTCCCCGACCGCCCGGTCCTTTCGCTG 3370                  3390                  3410
               .                     .                     .
        TTCACCGCACCTGATGTGTGGTACCCTGGCGGCATGGTGAGCAGAGTGCCCTATCCCAGT
        AAGTGGCGTGGACTACACACCATGGGACCGCCGTACCACTCGTCTCACGGGATAGGGTCA 3430                  3450                  3470
               .                     .                     .
        CCCACTTGTGTCAAAAGCGAAATGGGCCCCTGGATGGATAGCTACTCCGGACCTTACGGG
        GGGTGAACACAGTTTTCGCTTTACCCGGGGACCTACCTATCGATGAGGCCTGGAATGCCC 3490                  3510                  3530
               .                     .                     .
        GACATGCGTTTGGAGACTGCCAGGGACCATGTTTTGCCCATTGACTATTACTTTCCACCC
        CTGTACGCAAACCTCTGACGGTCCCTGGTACAAAACGGGTAACTGATAATGAAAGGTGGG 3550                  3570                  3590
               .                     .                     .
        CAGAAGACCTGCCTGATCTGTGGAGATGAAGCTTCTGGGTGTCACTATGGAGCTCTCACA
        GTCTTCTGGACGGACTAGACACCTCTACTTCGAAGACCCACAGTGATACCTCGAGAGTGT
```

*FIG. 4F*

```
                3610                    3630                    3650
                  .                       .                       .
         .        .        .        .        .        .        .        .
TGTGGAAGCTGCAAGGTCTTCTTCAAAAGAGCCGCTGAAGGGAAACAGAAGTACCTGTGC
ACACCTTCGACGTTCCAGAAGAAGTTTTCTCGGCGACTTCCCTTTGTCTTCATGGACACG 3670                    3690                    3710
                  .                       .                       .
         .        .        .        .        .        .        .        .
GCCAGCAGAAATGATTGCACTATTGATAAATTCCGAAGGAAAAATTGTCCATCTTGTCGT
CGGTCGTCTTTACTAACGTGATAACTATTTAAGGCTTCCTTTTTAACAGGTAGAACAGCA 3730                    3750                    3770
                  .                       .                       .
         .        .        .        .        .        .        .        .
CTTCGGAAATGTTATGAAGCAGGGATGACTCTGGGAGCCCGGAAGCTGAAGAAACTTGGT
GAAGCCTTTACAATACTTCGTCCCTACTGAGACCCTCGGGCCTTCGACTTCTTTGAACCA 3790                    3810                    3830
                  .                       .                       .
         .        .        .        .        .        .        .        .
AATCTGAAACTACAGGAGGAAGGAGAGGCTTCCAGCACCACCAGCCCCACTGAGGAGACA
TTAGACTTTGATGTCCTCCTTCCTCTCCGAAGGTCGTGGTGGTCGGGGTGACTCCTCTGT 3850                    3870                    3890
                  .                       .                       .
         .        .        .        .        .        .        .        .
ACCCAGAAGCTGACAGTGTCACACATTGAAGGCTATGAATGTCAGCCCATCTTTCTGAAT
TGGGTCTTCGACTGTCACAGTGTGTAACTTCCGATACTTACAGTCGGGTAGAAAGACTTA 3910                    3930                    3950
                  .                       .                       .
         .        .        .        .        .        .        .        .
GTCCTGGAAGCCATTGAGCCAGGTGTAGTGTGTGCTGGACACGACAACAACCAGCCCGAC
CAGGACCTTCGGTAACTCGGTCCACATCACACACGACCTGTGCTGTTGTTGGTCGGGCTG 3970                    3990                    4010
                  .                       .                       .
         .        .        .        .        .        .        .        .
TCCTTTGCAGCCTTGCTCTCTAGCCTCAATGAACTGGGAGAGAGACAGCTTGTACACGTG
AGGAAACGTCGGAACGAGAGATCGGAGTTACTTGACCCTCTCTGTCGAACATGTGCAC 4030                    4050                    4070
                  .                       .                       .
         .        .        .        .        .        .        .        .
GTCAAGTGGGCCAAGGCCTTGCCTGGCTTCCGCAACTTACACGTGGACGACCAGATGGCT
CAGTTCACCCGGTTCCGGAACGGACCGAAGGCGTTGAATGTGCACCTGCTGGTCTACCGA 4090                    4110                    4130
                  .                       .                       .
         .        .        .        .        .        .        .        .
GTCATTCAGTACTCCTGGATGGGGCTCATGGTGTTTGCCATGGGCTGGCGATCCTTCACC
CAGTAAGTCATGAGGACCTACCCCGAGTACCACAAACGGTACCCGACCGCTAGGAAGTGG 4150                    4170                    4190
                  .                       .                       .
         .        .        .        .        .        .        .        .
AATGTCAACTCCAGGATGCTCTACTTCGCCCCTGATCTGGTTTTCAATGAGTACCGCATG
TTACAGTTGAGGTCCTACGAGATGAAGCGGGGACTAGACCAAAAGTTACTCATGGCGTAC
```

FIG. 4G

```
           4210                    4230                    4250
             .                       .                       .
           .   .                   .   .                   .   .
CACAAGTCCCGGATGTACAGCCAGTGTGTCCGAATGAGGCACCTCTCTCAAGAGTTTGGA
GTGTTCAGGGCCTACATGTCGGTCACACAGGCTTACTCCGTGGAGAGAGTTCTCAAACCT 4270                    4290                    4310
             .                       .                       .
           .   .                   .   .                   .   .
TGGCTCCAAATCACCCCCCAGGAATTCCTGTGCATGAAAGCACTGCTACTCTTCAGCATT
ACCGAGGTTTAGTGGGGGGTCCTTAAGGACACGTACTTTCGTGACGATGAGAAGTCGTAA 4330                    4350                    4370
             .                       .                       .
           .   .                   .   .                   .   .
ATTCCAGTGGATGGGCTGAAAAATCAAAAATTCTTTGATGAACTTCGAATGAACTACATC
TAAGGTCACCTACCCGACTTTTTAGTTTTTAAGAAACTACTTGAAGCTTACTTGATGTAG 4390                    4410                    4430
             .                       .                       .
           .   .                   .   .                   .   .
AAGGAACTCGATCGTATCATTGCATGCAAAAGAAAAAATCCCACATCCTGCTCAAGACGC
TTCCTTGAGCTAGCATAGTAACGTACGTTTTCTTTTTTAGGGTGTAGGACGAGTTCTGCG 4450                    4470                    4490
             .                       .                       .
           .   .                   .   .                   .   .
TTCTACCAGCTCACCAAGCTCCTGGACTCCGTGCAGCCTATTGCGAGAGAGCTGCATCAG
AAGATGGTCGAGTGGTTCGAGGACCTGAGGCACGTCGGATAACGCTCTCTCGACGTAGTC 4510                    4530                    4550
             .                       .                       .
           .   .                   .   .                   .   .
TTCACTTTTGACCTGCTAATCAAGTCACACATGGTGAGCGTGGACTTTCCGGAAATGATG
AAGTGAAAACTGGACGATTAGTTCAGTGTGTACCACTCGCACCTGAAAGGCCTTTACTAC 4570                    4590                    4610
             .                       .                       .
           .   .                   .   .                   .   .
GCAGAGATCATCTCTGTGCAAGTGCCCAAGATCCTTTCTGGGAAAGTCAAGCCCATCTAT
CGTCTCTAGTAGAGACACGTTCACGGGTTCTAGGAAAGACCCTTTCAGTTCGGGTAGATA 4630                    4650                    4670
             .                       .                       .
           .   .                   .   .                   .   .
TTCCACACCCAGTGAAGCATTGGAAACCCTATTTCCCCACCCCAGCTCATGCCCCCTTTC
AAGGTGTGGGTCACTTCGTAACCTTTGGGATAAAGGGGTGGGGTCGAGTACGGGGGAAAG 4690                    4710                    4730
             .                       .                       .
           .   .                   .   .                   .   .
AGATGTCTTCTGCCTGTTATAACTCTGCACTACTCCTCTGCAGTGCCTTGGGGAATTTCC
TCTACAGAAGACGGACAATATTGAGACGTGATGAGGAGACGTCACGGAACCCCTTAAAGG 4750                    4770                    4790
             .                       .                       .
           .   .                   .   .                   .   .
TCTATTGATGTACAGTCTGTCATGAACATGTTCCTGAATTCTATTTGCTGGGCTTTTTTT
AGATAACTACATGTCAGACAGTACTTGTACAAGGACTTAAGATAAACGACCCGAAAAAAA
```

*FIG. 4H*

```
                    4810                    4830                    4850
                      .                       .                       .
          .           .           .           .           .           .
TTCTCTTTCTCTCCTTTCTTTTTCTTCTTCCCTCCCTATCTAACCCTCCCATGGCACCTT
AAGAGAAAGAGAGGAAAGAAAAAGAAGAAGGGAGGGATAGATTGGGAGGGTACCGTGGAA 4870                    4890                    4910
                      .                       .                       .
          .           .           .           .           .           .
CAGACTTTGCTTCCCATTGTGGCTCCTATCTGTGTTTTGAATGGTGTTGTATGCCTTTAA
GTCTGAAACGAAGGGTAACACCGAGGATAGACACAAAACTTACCACAACATACGGAAATT 4930                    4950                    4970
                      .                       .                       .
          .           .           .           .           .           .
ATCTGTGATGATCCTCATATGGCCCAGTGTCAAGTTGTGCTTGTTTACAGCACTACTCTG
TAGACACTACTAGGAGTATACCGGGTCACAGTTCAACACGAACAAATGTCGTGATGAGAC 4990                    5010                    5030
                      .                       .                       .
          .           .           .           .           .           .
TGCCAGCCACACAAACGTTTACTTATCTTATGCCACGGGAAGTTTAGAGAGCTAAGATTA
ACGGTCGGTGTGTTTGCAAATGAATAGAATACGGTGCCCTTCAAATCTCTCGATTCTAAT 5050                    5070
                      .                       .
          .           .           .           .
TCTGGGGAAATCAAAACAAAAAACAAGCAAACAAAAAAAAA
AGACCCCTTTAGTTTTGTTTTTTGTTCGTTTGTTTTTTTTT
```

FIG. 41

```
   1 GAGCTCTGGACAAAATTGAGCGCCTATGTGTACATGGCAAGTGTTTTAGTGTTTGTGTG
  61 TTTACCTGCTTGTCTGGGTGATTTTGCCTTTGAGAGTCTGGATGAGAAATGCATGGTTAA
 121 AGGCAATTCCAGACAGGAAGAAAGGCAGAGAAGAGGGTAGAAATGACCTCTGATTCTTGG
 181 GGCTGAGGGTTCCTAGAGCAAATGGCACAATGCCACGAGGCCCGATCTATCCCTATGACG
 241 GAACTCTAAGGTTTCAGCATCAGCTATCTGCTGGCTTGGTCACTGGCTTGCCTCCTCAGT
 301 TTGTAGGAGACTCTCCCACTCTCCCATCTGCGCGCTCTTATCAGTCCTGAAAAGAACCCN
 361 TGGCNAGCCAGGAGCNAGGTATTCNTATCGTCCTTTTCNTCCTCCTNGCCTCACCTNGTT
 421 GNTTTTTAGATTGGNCTTNGNAACCAAATTTGTATGCTGGCCTCCAGGAAATCTGGAGCC
 481 TGGCGCCTAAACCTTGGTTTAGGAAAGCAGGAGCTATTCAGGAAGCAGGGTCCTCCAGGG
 541 CTAGAGCTAGCCTCTCCTGCCCTCGCCCACGTGCGCCAGCACTTGTTTCTCCAAAGCNAC
 601 TAGGCAGGCGTTAGCGCGCGGTGAGGGGAGGGGAGAAAAGGAAAGGGGAGGGGAGGGAAA
 661 AGGAGGTGGGAAGGCAAGGAGGCCGGCCNGGTGGGGCGGGACCCGACTCGCANNAACTG
 721 TTGCATTTGCTCTCCACCTCCCAGCGCCCCCTCCGAGATCCCGGGGAGCCAGCTTGCTGG
 781 GAGAGCGGGAACGGTCCGGAGCAAGCCCAGAGGCAGAGGAGGCGACAGAGGGAAAAAGGG
 841 CCCNAGCTAGCCGCTCCAGTGCTGTACAGNAGCCGAAGGACGCACCACGCCAGCCCCAGC
 901 CCGGCTCCAGCGACAGCNAACGCCTCTTGCANGCGTTCGAAGCCGCCGCCCGGAGCTGCC
 961 CTTTCCTCTTCGGTGAAGTTTTTAAAAGCTGCTAAAGACTCGGAGGAAGCAAGGAAAGTG
1021 CCTGGTAGGACTGACGGCTGCCTTTGTCCTCCTCCTCTCCACCCCGCCTCCCCCCACCCT
1081 GCCTTCCCCCCCTCCCCCGTCTTCTCTCCCGCAGCTGCCTCAGTCGGCTACTCTCAGCCA
1141 ACCCCCCTCACCACCCTTCTCCCCACCCGCCCCCCGCCCCCGTCGGCCCAGCGNTGNCA
1201 GNCCGAGTTTGCAGAGAGGTAACTCCCTTTGGCTGCGAGCGGGCGAGNCTAGCTGCACAT
1261 TGCAAAGAAGGCTCTTAGGAGCAGGCGACTGGGGAGCGGCTTCAGCACTGCAGCCACGAC
1321 CNGCCTGGTTAGGCTGCACGCGGAGAGAACCCTCTGTTTTCCCCACTCTCTCTCCACCT
1381 CCTCCTGCCTTCCCCACCCCGAGTGCGGAGCCAGAGATCAAAAGATGAAAAGGCAGTCAG
1441 GTCTTCAGTAGCCAAAAAACAAAACAAACAAAAACAAAAAGCCGAAATAAAAGAAAAAG
```

*FIG. 5A*

```
1501 ATAATAACTCAGTTCTTATTTGCACCTACTTCAGTGGACACTGAATTTGGAAGGTGGAGG

1561 ATTTTGTTTTTTCTTTTAAGATCTGGGCATCTTTTGAATCTACCCTTCAAGTATTAAGA

1621 GACAGACTGTGAGCCTAGCAGGGCAGATCTTGTCCACCGTGTGTCTTCTTCTGCACGAGA

1681 CTTTGAGGCTGTCAGAGCGCTTTTGCGTGGTTGCTCCCGCAAGTTTCCTTCTCTGGAGC

1741 TTCCCGCAGGTGGGCAGCTAGCTGCAGCGACTACCGCATCATCACAGCCTGTTGAACTCT

1801 TCTGAGCAAGAGAAGGGGAGGCGGGGTAAGGGAAGTAGGTGGAAGATTCAGCCAAGCTCA

1861 AGGATGGAAGTGCAGTTAGGGCTGGGAAGGGTCTACCCTCGGCCGCCGTCCAAGACCTAC
        MetGluValGlnLeuGlyLeuGlyArgValTyrProArgProProSerLysThrTyr

1921 CGAGGAGCTTTCCAGAATCTGTTCCAGAGCGTGCGCGAAGTGATCCAGAACCCGGGCCCC
     ArgGlyAlaPheGlnAsnLeuPheGlnSerValArgGluValIleGlnAsnProGlyPro

1981 AGGCACCCAGAGGCCGCGAGCGCAGCACCTCCCGGCGCCAGTTTGCTGCTGCTGCAGCAG
     ArgHisProGluAlaAlaSerAlaAlaProProGlyAlaSerLeuLeuLeuLeuGlnGln

2041 CAGCAGCAGCAGCAGCAGCAGCAGCAGCAGCAGCAGCAGCAGCAGCAGCAGCAGCAGCAG
     GlnGlnGlnGlnGlnGlnGlnGlnGlnGlnGlnGlnGlnGlnGlnGlnGlnGlnGlnGln

2101 CAGCAGCAAGAGACTAGCCCCAGGCAGCAGCAGCAGCAGCAGGGTGAGGATGGTTCTCCC
     GlnGlnGlnGluThrSerProArgGlnGlnGlnGlnGlnGlnGlyGluAspGlySerPro

2161 CAAGCCCATCGTAGAGGCCCCACAGGCTACCTGGTCCTGGATGAGGAACAGCAACCTTCA
     GlnAlaHisArgArgGlyProThrGlyTyrLeuValLeuAspGluGluGlnGlnProSer

2221 CAGCCGCAGTCGGCCCTGGAGTGCCACCCCGAGAGAGGTTGCGTCCCAGAGCCTGGAGCC
     GlnProGlnSerAlaLeuGluCysHisProGluArgGlyCysValProGluProGlyAla

2281 GCCGTGGCCGCCAGCAAGGGGCTGCCGCAGCAGCTGCCAGCACCTCCGGACGAGGATGAC
     AlaValAlaAlaSerLysGlyLeuProGlnGlnLeuProAlaProProAspGluAspAsp

2341 TCAGCTGCCCCATCCACGTTGTCCCTGCTGGGCCCCACTTTCCCCGGCTTAAGCAGCTGC
     SerAlaAlaProSerThrLeuSerLeuLeuGlyProThrPheProGlyLeuSerSerCys

2401 TCCGCTGACCTTAAAGACATCCTGAGCGAGGCCAGCACCATGCAACTCCTTCAGCAACAG
     SerAlaAspLeuLysAspIleLeuSerGluAlaSerThrMetGlnLeuLeuGlnGlnGln

2461 CAGCAGGAAGCAGTATCCGAAGGCAGCAGCAGCGGGAGAGCGAGGGAGGCCTCGGGGGCT
     GlnGlnGluAlaValSerGluGlySerSerSerGlyArgAlaArgGluAlaSerGlyAla

2521 CCCACTTCCTCCAAGGACAATTACTTAGGGGGCACTTCGACCATTTCTGACAACGCCAAG
     ProThrSerSerLysAspAsnTyrLeuGlyGlyThrSerThrIleSerAspAsnAlaLys
```

*FIG. 5B*

2581 GAGTTGTGTAAGGCAGTGTCGGTGTCCATGGGCCTGGGTGTGGAGGCGTTGGAGCATCTG
GluLeuCysLysAlaValSerValSerMetGlyLeuGlyValGluAlaLeuGluHisLeu

2641 AGTCCAGGGGAACAGCTTCGGGGGGATTGCATGTACGCCCCACTTTTGGGAGTTCCACCC
SerProGlyGluGlnLeuArgGlyAspCysMetTyrAlaProLeuLeuGlyValProPro

2701 GCTGTGCGTCCCACTCCTTGTGCCCCATTGGCCGAATGCAAAGGTTCTCTGCTAGACGAC
AlaValArgProThrProCysAlaProLeuAlaGluCysLysGlySerLeuLeuAspAsp

2761 AGCGCAGGCAAGAGCACTGAAGATACTGCTGAGTATTCCCCTTTCAAGGGAGGTTACACC
SerAlaGlyLysSerThrGluAspThrAlaGluTyrSerProPheLysGlyGlyTyrThr

2821 AAAGGGCTAGAAGGCGAGAGCCTAGGCTGCTCTGGCAGCGCTGCAGCAGGGAGCTCCGGG
LysGlyLeuGluGlyGluSerLeuGlyCysSerGlySerAlaAlaAlaGlySerSerGly

2881 ACACTTGAACTGCCGTCTACCCTGTCTCTCTACAAGTCCGGAGCACTGGACGAGGCAGCT
ThrLeuGluLeuProSerThrLeuSerLeuTyrLysSerGlyAlaLeuAspGluAlaAla

2941 GCGTACCAGAGTCGCGACTACTACAACTTTCCACTGGCTCTGGCCGGACCGCCGCCCCCT
AlaTyrGlnSerArgAspTyrTyrAsnPheProLeuAlaLeuAlaGlyProProProPro

3001 CCGCCGCCTCCCCATCCCCACGCTCGCATCAAGCTGGAGAACCCGCTGGACTACGGCAGC
ProProProProHisProHisAlaArgIleLysLeuGluAsnProLeuAspTyrGlySer

3061 GCCTGGGCGGCTGCGGCGGCGCAGTGCCGCTATGGGGACCTGGCGAGCCTGCATGGCGCG
AlaTrpAlaAlaAlaAlaAlaGlnCysArgTyrGlyAspLeuAlaSerLeuHisGlyAla

3121 GGTGCAGCGGGACCCGGTTCTGGGTCACCCTCAGCCGCCGCTTCCTCATCCTGGCACACT
GlyAlaAlaGlyProGlySerGlySerProSerAlaAlaAlaSerSerSerTrpHisThr

3181 CTCTTCACAGCCGAAGAAGGCCAGTTGTATGGACCGTGTGGTGGTGGTGGGGGTGGTGGC
LeuPheThrAlaGluGluGlyGlnLeuTyrGlyProCysGlyGlyGlyGlyGlyGlyGly

3241 GGCGGCGGCGGCGGCGGCGGCGGCGGCGGCGGCGGCGGCGGCGGCGGCGAGGCGGGA
GlyGlyGlyGlyGlyGlyGlyGlyGlyGlyGlyGlyGlyGlyGlyGlyGluAlaGly

3301 GCTGTAGCCCCCTACGGCTACACTCGGCCCCCTCAGGGGCTGGCGGGCCAGGAAAGCGAC
AlaValAlaProTyrGlyTyrThrArgProProGlnGlyLeuAlaGlyGlnGluSerAsp

3361 TTCACCGCACCTGATGTGTGGTACCCTGGCGGCATGGTGAGCAGAGTGCCCTATCCCAGT
PheThrAlaProAspValTrpTyrProGlyGlyMetValSerArgValProTyrProSer

3421 CCCACTTGTGTCAAAAGCGAAATGGGCCCCTGGATGGATAGCTACTCCGGACCTTACGGG
ProThrCysValLysSerGluMetGlyProTrpMetAspSerTyrSerGlyProTyrGly

3481 GACATGCGTTTGGAGACTGCCAGGGACCATGTTTTGCCCATTGACTATTACTTTCCACCC
AspMetArgLeuGluThrAlaArgAspHisValLeuProIleAspTyrTyrPheProPro

FIG. 5C

```
3541 CAGAAGACCTGCCTGATCTGTGGAGATGAAGCTTCTGGGTGTCACTATGGAGCTCTCACA
     GlnLysThrCysLeuIleCysGlyAspGluAlaSerGlyCysHisTyrGlyAlaLeuThr

3601 TGTGGAAGCTGCAAGGTCTTCTTCAAAAGAGCCGCTGAAGGGAAACAGAAGTACCTGTGC
     CysGlySerCysLysValPhePheLysArgAlaAlaGluGlyLysGlnLysTyrLeuCys

3661 GCCAGCAGAAATGATTGCACTATTGATAAATTCCGAAGGAAAAATTGTCCATCTTGTCGT
     AlaSerArgAsnAspCysThrIleAspLysPheArgArgLysAsnCysProSerCysArg

3721 CTTCGGAAATGTTATGAAGCAGGGATGACTCTGGGAGCCCGGAAGCTGAAGAAACTTGGT
     LeuArgLysCysTyrGluAlaGlyMetThrLeuGlyAlaArgLysLeuLysLysLeuGly

3781 AATCTGAAACTACAGGAGGAAGGAGAGGCTTCCAGCACCACCAGCCCCACTGAGGAGACA
     AsnLeuLysLeuGlnGluGluGlyGluAlaSerSerThrThrSerProThrGluGluThr

3841 ACCCAGAAGCTGACAGTGTCACACATTGAAGGCTATGAATGTCAGCCCATCTTTCTGAAT
     ThrGlnLysLeuThrValSerHisIleGluGlyTyrGluCysGlnProIlePheLeuAsn

3901 GTCCTGGAAGCCATTGAGCCAGGTGTAGTGTGTGCTGGACACGACAACAACCAGCCCGAC
     ValLeuGluAlaIleGluProGlyValValCysAlaGlyHisAspAsnAsnGlnProAsp

3961 TCCTTTGCAGCCTTGCTCTCTAGCCTCAATGAACTGGGAGAGAGACAGCTTGTACACGTG
     SerPheAlaAlaLeuLeuSerSerLeuAsnGluLeuGlyGluArgGlnLeuValHisVal

4021 GTCAAGTGGGCCAAGGCCTTGCCTGGCTTCCGCAACTTACACGTGGACGACCAGATGGCT
     ValLysTrpAlaLysAlaLeuProGlyPheArgAsnLeuHisValAspAspGlnMetAla

4081 GTCATTCAGTACTCCTGGATGGGGCTCATGGTGTTTGCCATGGGCTGGCGATCCTTCACC
     ValIleGlnTyrSerTrpMetGlyLeuMetValPheAlaMetGlyTrpArgSerPheThr

4141 AATGTCAACTCCAGGATGCTCTACTTCGCCCCTGATCTGGTTTTCAATGAGTACCGCATG
     AsnValAsnSerArgMetLeuTyrPheAlaProAspLeuValPheAsnGluTyrArgMet

4201 CACAAGTCCCGGATGTACAGCCAGTGTGTCCGAATGAGGCACCTCTCTCAAGAGTTTGGA
     HisLysSerArgMetTyrSerGlnCysValArgMetArgHisLeuSerGlnGluPheGly

4261 TGGCTCCAAATCACCCCCCAGGAATTCCTGTGCATGAAAGCACTGCTACTCTTCAGCATT
     TrpLeuGlnIleThrProGlnGluPheLeuCysMetLysAlaLeuLeuLeuPheSerIle

4321 ATTCCAGTGGATGGGCTGAAAAATCAAAAATTCTTTGATGAACTTCGAATGAACTACATC
     IleProValAspGlyLeuLysAsnGlnLysPhePheAspGluLeuArgMetAsnTyrIle

4381 AAGGAACTCGATCGTATCATTGCATGCAAAAGAAAAAATCCCACATCCTGCTCAAGACGC
     LysGluLeuAspArgIleIleAlaCysLysArgLysAsnProThrSerCysSerArgArg

4441 TTCTACCAGCTCACCAAGCTCCTGGACTCCGTGCAGCCTATTGCGAGAGAGCTGCATCAG
     PheTyrGlnLeuThrLysLeuLeuAspSerValGlnProIleAlaArgGluLeuHisGln
```

*FIG. 5D*

```
4501 TTCACTTTTGACCTGCTAATCAAGTCACACATGGTGAGCGTGGACTTTCCGGAAATGATG
     PheThrPheAspLeuLeuIleLysSerHisMetValSerValAspPheProGluMetMet

4561 GCAGAGATCATCTCTGTGCAAGTGCCCAAGATCCTTTCTGGGAAAGTCAAGCCCATCTAT
     AlaGluIleIleSerValGlnValProLysIleLeuSerGlyLysValLysProIleTyr

4621 TTCCACACCCAGTGAAGCATTGGAAACCCTATTTCCCCACCCCAGCTCATGCCCCCTTTC
     PheHisThrGlnEnd

4681 AGATGTCTTCTGCCTGTTATAACTCTGCACTACTCCTCTGCAGTGCCTTGGGGAATTTCC

4741 TCTATTGATGTACAGTCTGTCATGAACATGTTCCTGAATTCTATTTGCTGGGCTTTTTTT

4801 TTCTCTTTCTCTCCTTTCTTTTTCTTCTTCCCTCCCTATCTAACCCTCCCATGGCACCTT

4861 CAGACTTTGCTTCCCATTGTGGCTCCTATCTGTGTTTTGAATGGTGTTGTATGCCTTTAA

4921 ATCTGTGATGATCCTCATATGGCCCAGTGTCAAGTTGTGCTTGTTTACAGCACTACTCTG

4981 TGCCAGCCACACAAACGTTTACTTATCTTATGCCACGGGAAGTTTAGAGAGCTAAGATTA

5041 TCTGGGGAAATCAAAACAAAAAACAAGCAAACAAAAAAAAAA 5082
```

*FIG. 5E*

```
AATTCGGGAAGGATCGAGCAAACCAGGAAAGTAAGGATGGAGATCCTAGGAGAGTGTCCA    60

TGCCTCGAAAGGAGCCCACCAAAGATGAACTGTTGCATTTGCTTTCCACCTCCCAGCGCC   120

CCCTCGGAGATCCCTAGGAGCCAGCCTGCTGGGAGAACCAGAGGGTCCGGAGCAAACCTG   180

GAGGCTGAGAGGGCATCAGAGGGGAAAAGACTGAGTTAGCCACTCCAGTGCCATACAGAA   240

GCTTAAGGGACATACCACGCCAGCCCCAGCCCAGCGACAGCCAACGCCTGTTGCAGAGCG   300

GCGGCTTCGAAGCCGCCGCCCAGAAGCTGCCCTTTCCTCTTCGGTGAAGTTTCTAAAAGC   360

TGCGGGAGACTCGGAGGAAGCGAAGAAAGTGTCCGGTAGGACTACGACTGCCTTTGTCCT   420

CCTCCCTCCTACCCCTACCCCTCCTGGGTCCCCTCTCCCTGAGCGGACTAGGCAGGCTTC   480

CTGGCCAGCCCTCTCCCCTACACCACCAGCTCTGCCAGCCAGTTTGCACAGAGGTAACTC   540

CCTTTGGCTGAAAGCAGACGAGCTTGTTGCCCATTGGAAGGGAGGCTTTTGGGAGCCCAG   600

AGACTGAGGAGCAACAGCACGCTGGAGAGTCCCTGATTCCAGGTTCTCCCCCCTGCACCT   660

CCTACTGCCCGCCCCTCACCCTGTGTGTGCAGCTAGAATTGAAAAGATGAAAAGACAGTT   720

GGGGCTTCAGTAGTCGAAAGCAAAACAAAAGCAAAAAGAAAACAAAAAGAAAATAGCCCA   780

GTTCTTATTTGCACCTGCTTCAGTGGACATTGACTTTGGAAGGCAGAGAATTTTCCTTCC   840

CCCCAGTCAAGCTTTGAGCATCTTTTAATCTGTTCTTCAAGTATTTAGGGACAAACTGTG   900

AAACTAGCAGGGCAGATCCTGTCTAGCGCGTGCCTTCCTTTACAGGAGACTTTGAGGCTA   960

TCTGGGCGCTCCCCCCCCTCCCTGCAAGTTTTCTTCCCTGGAGCTTCCCGCAGGTGGGCA  1020

GCTAGCTGCAGATACTACATCATCAGTCAGTAGAACTCTTCAGAGCAAGAGACGAGGAGG  1080

CAGGATAAGGGAATTCGGTGGAAGCTAGAGACAAGCTAAAGGATGGAGGTGCAGTTAGGG  1140
                                            MetGluValGlnLeuGly

CTGGGAAGGGTCTACCCACGGCCCCCGTCCAAGACCTATCGAGGAGCGTTCCAGAATCTG  1200
LeuGlyArgValTyrProArgProProSerlysThrTyrArgGlyAlaPheGlnAsnLeu TTCCAGAGCGTGCGCGAAGCGATCCAGAACCCGGGCCCCAGGCACCCTGAGGCCGCTAGC  1260
PheGlnSerValArgGluAlaIleGlnAsnProGlyProArgHisProGluAlaAlaSer ATAGCACCTCCCGGTGCCTGTTTACAGCAGCGGCAGGAGACTAGCCCCGGCGGCGGCGG  1320
IleAlaProProGlyAlaCysLeuGlnGlnArgGlnGluThrSerProArgArgArgArg CGGCAGCAGCACCCTGAGGATGGCTCTCCTCAAGCCCACATCAGAGGCACCACAGGCTAC  1380
ArgGlnGlnHisProGluAspGlySerProGlnAlaHisIleArgGlyThrThrGlyTyr
```

*FIG. 6A*

```
CTGGCCCTGGAGGAGGAACAGCAGCCTTCACAGCAGCAGTCAGCCTCCGAGGGCCACCCT   1440
LeuAlaLeuGluGluGluGlnGlnProSerGlnGlnGlnSerAlaSerGluGlyHisPro

GAGAGCGGCTGCCTCCCGGAGCCTGGAGCTGCCACGGCTCCTGGCAAGGGGCTGCCGCAG   1500
GluSerGlyCysLeuProGluProGlyAlaAlaThrAlaProGlyLysGlyLeuProGln

CAGCCACCAGCTCCTCCAGATCAGGATGACTCAGCTGCCCCATCCACGTTGTCCCTACTG   1560
GlnProProAlaProProAspGlnAspAspSerAlaAlaProSerThrLeuSerLeuLeu

GGCCCCACTTTCCCAGGCTTAAGCAGCTGCTCCGCAGACATTAAAGACATCCTGAGCGAG   1620
GlyProThrPheProGlyLeuSerSerCysSerAlaAspIleLysAspIleLeuSerGlu

GCCGGCACCATGCAACTTCTTCAGCAGCAGCAGCAACAGCAACAGCAGCAGCAGCAGCAG   1680
AlaGlyThrMetGlnLeuLeuGlnGlnGlnGlnGlnGlnGlnGlnGlnGlnGlnGlnGln

CAGCAGCAGCAGCAGCAACAGCAGCAGGAGGTAATATCCGAAGGCAGCAGCAGCGTGAGA   1740
GlnGlnGlnGlnGlnGlnGlnGlnGluValIleSerGluGlySerSerSerValArg

GCAAGGGAGGCCACTGGGGCTCCCTCTTCCTCCAAGGATAGTTACCTAGGGGGCAATTCG   1800
AlaArgGluAlaThrGlyAlaProSerSerSerLysAspSerTyrLeuGlyGlyAsnSer

ACCATATCTGACAGTGCCAAGGAGTTGTGTAAAGCAGTGTCTGTGTCCATGGGGTTGGGT   1860
ThrIleSerAspSerAlaLysGluLeuCysLysAlaValSerValSerMetGlyLeuGly

GTGGAAGCACTGGAACATCTGAGTCCAGGGGAGCAGCTTCGGGGCGACTGCATGTACGCG   1920
ValGluAlaLeuGluHisLeuSerProGlyGluGlnLeuArgGlyAspCysMetTyrAla

TCGCTCCTGGGAGGTCCACCCGCCGTGCGTCCCACTCCTTGTGCGCCTCTGGCCGAATGC   1980
SerLeuLeuGlyGlyProProAlaValArgProThrProCysAlaProLeuAlaGluCys

AAAGGTCTTTCCCTGGACGAAGGCCCGGGCAAAGGCACTGAAGAGACTGCTGAGTATTCC   2040
LysGlyLeuSerLeuAspGluGlyProGlyLysGlyThrGluGluThrAlaGluTyrSer

TCTTTCAAGGGAGGTTACGCCAAAGGGTTGGAAGGTGAGAGTCTGGGCTGCTCTGGCAGC   2100
SerPheLysGlyGlyTyrAlaLysGlyLeuGluGlyGluSerLeuGlyCysSerGlySer

AGTGAAGCAGGTAGCTCTGGGACACTTGAGATCCCGTCCTCACTGTCTCTGTATAAGTCT   2160
SerGluAlaGlySerSerGlyThrLeuGluIleProSerSerLeuSerLeuTyrLysSer

GGAGCAGTAGACGAGGCAGCAGCATACCAGAATCGCGACTACTACAACTTTCCGCTCGCT   2220
GlyAlaValAspGluAlaAlaAlaTyrGlnAsnArgAspTyrTyrAsnPheProLeuAla

CTGTCCGGGCCGCCGCACCCCCCGCCCCCTACCCATCCACACGCCCGCATCAAGCTGGAG   2280
LeuSerGlyProProHisProProProThrHisProHisAlaArgIleLysLeuGlu

AACCCGTCGGACTACGGCAGCGCCTGGGCTGCGGCGGCAGCGCAATGCCGCTATGGGGAC   2340
AsnProSerAspTyrGlySerAlaTrpAlaAlaAlaAlaAlaGlnCysArgTyrGlyAsp

TTGGCTAGCCTACATGGAGGGAGTGTAGCCGGACCCAGCACTGGATCGCCCCAGCCACC   2400
LeuAlaSerLeuHisGlyGlySerValAlaGlyProSerThrGlySerProProAlaThr
```

*FIG. 6B*

```
GCCTCTTCTTCCTGGCATACTCTCTTCACAGCTGAAGAAGGCCAATTATATGGGCCAGGA  2460
AlaSerSerSerTrpHisThrLeuPheThrAlaGluGluGlyGlnLeuTyrGlyProGly

GGCGGGGGCGGCAGCAGTAGCCCAAGCGATGCTGGGCCTGTAGCCCCCTATGGCTACACT  2520
GlyGlyGlyGlySerSerSerProSerAspAlaGlyProValAlaProTyrGlyTyrThr

CGGCCCCCTCAGGGGCTGGCAAGCCAGGAGGGTGACTTCTCTGCCTCTGAAGTGTGGTAT  2580
ArgProProGlnGlyLeuAlaSerGlnGluGlyAspPheSerAlaSerGluValTrpTyr

CCTGGTGGAGTTGTGAACAGAGTCCCCTATCCCAGTCCCAGTTGTGTTAAAAGTGAAATG  2640
ProGlyGlyValValAsnArgValProTyrProSerProSerCysValLysSerGluMet

GGACCTTGGATGGAGAACTACTCCGGACCTTATGGGGACATGCGTTTGGACAGTACCAGG  2700
GlyProTrpMetGluAsnTyrSerGlyProTyrGlyAspMetArgLeuAspSerThrArg

GACCACGTTTTACCCATCGACTATTACTTCCCACCCCAGAAGACCTGCCTGATCTGTGGA  2760
AspHisValLeuProIleAspTyrTyrPheProProGlnLysThrCysLeuIleCysGly

GATGAAGCTTCTGGTTGTCACTACGGAGCTCTCACTTGTGGCAGCTGCAAGGTCTTCTTC  2820
AspGluAlaSerGlyCysHisTyrGlyAlaLeuThrCysGlySerCysLysValPhePhe

AAAAGAGCTGCGGAAGGGAAACAGAAGTATCTATGTGCCAGCAGAAATGATTGCACCATT  2880
LysArgAlaAlaGluGlyLysGlnLysTyrLeuCysAlaSerArgAsnAspCysThrIle

GATAAATTTCGGAGGAAAAATTGTCCATCGTGTCGTCTCCGGAAATGTTATGAAGCAGGG  2940
AspLysPheArgArgLysAsnCysProSerCysArgLeuArgLysCysTyrGluAlaGly

ATGACTCTGGGAGCTCGTAAGCTGAAGAAACTTGGAAATCTCAAACTACAGGAAGAAGGA  3000
MetThrLeuGlyAlaArgLysLeuLysLysLeuGlyAsnLeuLysLeuGlnGluGluGly

GAAAACTCCAGTGCTGGTAGCCCCACTGAGGACCCATCCCAGAAGATGACTGTATCACAC  3060
GluAsnSerSerAlaGlySerProThrGluAspProSerGlnLysMetThrValSerHis

ATTGAAGGCTATGAATGTCAACCTATCTTTCTTAATGTCCTGGAAGCCATTGAGCCAGGA  3120
IleGluGlyTyrGluCysGlnProIlePheLeuAsnValLeuGluAlaIleGluProGly

GTGGTGTGTGCCGGACATGACAACAACCAGCCTGATTCCTTTGCTGCCTTGTTATCTAGT  3180
ValValCysAlaGlyHisAspAsnAsnGlnProAspSerPheAlaAlaLeuLeuSerSer

CTCAACGAGCTTGGCGAGAGACAGCTTGTACATGTGGTCAAGTGGGCCAAGGCCTTGCCT  3240
LeuAsnGluLeuGlyGluArgGlnLeuValHisValValLysTrpAlaLysAlaLeuPro

GGCTTCCGCAACTTGCATGTGGATGACCAGATGGCAGTCATTCAGTATTCCTGGATGGGA  3300
GlyPheArgAsnLeuHisValAspAspGlnMetAlaValIleGlnTyrSerTrpMetGly

CTGATGGTATTTGCCATGGGTTGGCGGTCCTTCACTAATGTCAACTCTAGGATGCTCTAC  3360
LeuMetValPheAlaMetGlyTrpArgSerPheThrAsnValAsnSerArgMetLeuTyr

TTTGCACCTGACCTGGTTTTCAATGAGTATCGCATGCACAAGTCTCGAATGTACAGCCAG  3420
PheAlaProAspLeuValPheAsnGluTyrArgMetHisLysSerArgMetTyrSerGln
```

*FIG. 6C*

```
TGCGTGAGGATGAGGCACCTTTCTCAAGAGTTTGGATGGCTCCAGATAACCCCCCAGGAA    3480
CysValArgMetArgHisLeuSerGlnGluPheGlyTrpLeuGlnIleThrProGlnGlu

TTCCTGTGCATGAAAGCACTGCTACTCTTCAGCATTATTCCAGTGGATGGGCTGAAAAAT    3540
PheLeuCysMetLysAlaLeuLeuLeuPheSerIleIleProValAspGlyLeuLysAsn

CAAAAATTCTTTGATGAACTTCGAATGAACTACATCAAGGAACTTGATCGCATCATTGCA    3600
GlnLysPhePheAspGluLeuArgMetAsnTyrIleLysGluLeuAspArgIleIleAla

TGCAAAAGAAAAAATCCCACATCCTGCTCAAGGCGCTTCTACCAGCTCACCAAGCTCCTG    3660
CysLysArgLysAsnProThrSerCysSerArgArgPheTyrGlnLeuThrLysLeuLeu

GATTCTGTGCAGCCTATTGCAAGAGAGCTGCATCAATTCACTTTTGACCTGCTAATCAAG    3720
AspSerValGlnProIleAlaArgGluLeuHisGlnPheThrPheAspLeuLeuIleLys

TCCCATATGGTGAGCGTGGACTTTCCTGAAATGATGGCAGAGATCATCTCTGTGCAAGTG    3780
SerHisMetValSerValAspPheProGluMetMetAlaGluIleIleSerValGlnVal

CCCAAGATCCTTTCTGGGAAAGTCAGCCCATGTATTTCCACACACAGTGAAGATTTGGAA    3840
ProLysIleLeuSerGlyLysValSerProCysIleSerThrHisSerGluAspLeuGlu

CCTAATACCCAAACCCACCTGTTCCCTTTTCAGATGTCTTCTGCCTGTTATATAACTCTG    3900
ProAsnThrGlnThrHisLeuPheProPheGlnMetSerSerAlaCysTyrIleThrLeu

CACTACTTCTCTGGCATGGGCCTTGGGGGAAATTCCTCTACTGATGTACAGTCTGTCATG    3960
HisTyrPheSerGlyMetGlyLeuGlyGlyAsnSerSerThrAspValGlnSerValMet

AACATGTTCCCCAAGTTCTATTTCCTGGGCTTTTCCTTCTTTCTTTTTCTTCTTCTCTGC    4020
AsnMetPheProLysPheTyrPheLeuGlyPheSerPhePheLeuPheLeuLeuLeuCys

CTCTTTTACCCTCCCATGGCACATTTTGAATCCGCTGCGTGTTGTGGCTCCTGCCTGTGT    4080
LeuPheTyrProProMetAlaHisPheGluSerAlaAlaCysCysGlySerCysLeuCys

TTTGAGTTTTGTTGTATTTCTTCAAGTCTGTGATGATCTTCTTGTGGCCCAGTGTCAACT    4140
PheGluPheCysCysIleSerSerSerLeuEnd

GTGCTTGTTTATAGCACTGTGCTGTGTGCCAACCAAGCAAATGTTTACTCACCTTATGCC    4200

ATGGCAAGTTTAGAGAGCTATAAGTATCTTGGGAAGAAACAAACAGAGAGAGTAAAAAAA    4260

CCAAAAAAAAAAAAAAAAAAACCGAATTC                                  4288
```

*FIG. 6D*

SEQUENCE LISTING

```
<160> NUMBER OF SEQ ID NOS: 26

<210> SEQ ID NO 1
<211> LENGTH: 32
<212> TYPE: DNA
<213> ORGANISM: Artificial sequence
<220> FEATURE:
<223> OTHER INFORMATION: Synthetic oligonucleotide probe

<400> SEQUENCE: 1
acctgtgagg gctgtaaggt cttcttcaaa ag                               32

<210> SEQ ID NO 2
<211> LENGTH: 32
<212> TYPE: DNA
<213> ORGANISM: Homo sapiens

<400> SEQUENCE: 2
acatgtggaa gctgcaaggt cttcttcaaa ag                               32

<210> SEQ ID NO 3
<211> LENGTH: 32
<212> TYPE: DNA
```

-continued

<213> ORGANISM: Homo sapiens

<400> SEQUENCE: 3
acctgtggga gctgtaaggt cttctttaag ag         32

<210> SEQ ID NO 4
<211> LENGTH: 32
<212> TYPE: DNA
<213> ORGANISM: Homo sapiens

<400> SEQUENCE: 4
acctgtggca gctgcaaagt tttcttcaaa ag         32

<210> SEQ ID NO 5
<211> LENGTH: 32
<212> TYPE: DNA
<213> ORGANISM: Homo sapiens

<400> SEQUENCE: 5
acttgtggaa gctgtaaagt tttcttcaaa ag         32

<210> SEQ ID NO 6
<211> LENGTH: 32
<212> TYPE: DNA
<213> ORGANISM: Homo sapiens

<400> SEQUENCE: 6
tcctgtgagg gctgtaaggc cttcttcaag ag         32

<210> SEQ ID NO 7
<211> LENGTH: 32
<212> TYPE: DNA
<213> ORGANISM: Homo sapiens

<400> SEQUENCE: 7
acgtgtgaag gctgcaaggg tttctttaga ag         32

<210> SEQ ID NO 8
<211> LENGTH: 32
<212> TYPE: DNA
<213> ORGANISM: Homo sapiens

<400> SEQUENCE: 8
gcctgtgagg gctgcaaggg cttcttccgc cg         32

<210> SEQ ID NO 9
<211> LENGTH: 66
<212> TYPE: PRT
<213> ORGANISM: Homo sapiens

<400> SEQUENCE: 9

Cys Leu Ile Cys Gly Asp Glu Ala Ser Gly Cys His Tyr Gly Ala Leu
1               5                   10                  15

Thr Cys Gly Ser Cys Lys Val Phe Phe Lys Arg Ala Ala Glu Gly Lys
            20                  25                  30

Gln Lys Tyr Leu Cys Ala Ser Arg Asn Asp Cys Thr Ile Asp Lys Phe
        35                  40                  45

Arg Arg Lys Asn Cys Pro Ser Cys Arg Leu Arg Lys Cys Tyr Glu Ala
    50                  55                  60

Gly Met
65

<210> SEQ ID NO 10
<211> LENGTH: 66
<212> TYPE: PRT
<213> ORGANISM: Homo sapiens

<400> SEQUENCE: 10

Cys Leu Ile Cys Gly Asp Glu Ala Ser Gly Cys His Tyr Gly Val Leu
1               5                   10                  15

Thr Cys Gly Ser Cys Lys Val Phe Phe Lys Arg Ala Met Glu Gly Gln
            20                  25                  30

His Asn Tyr Leu Cys Ala Gly Arg Asn Asp Cys Ile Val Asp Lys Ile
        35                  40                  45

Arg Arg Lys Asn Cys Pro Ala Cys Arg Leu Arg Lys Cys Cys Gln Ala
    50                  55                  60

Gly Met
65

<210> SEQ ID NO 11
<211> LENGTH: 66
<212> TYPE: PRT
<213> ORGANISM: Homo sapiens

<400> SEQUENCE: 11

Cys Leu Val Cys Gly Asp Glu Ala Ser Gly Cys His Tyr Gly Val Val
1               5                   10                  15

Thr Cys Gly Ser Cys Lys Val Phe Phe Lys Arg Ala Val Glu Gly Gln
            20                  25                  30

His Asn Tyr Leu Cys Ala Gly Arg Asn Asp Cys Ile Ile Asp Lys Ile
        35                  40                  45

Arg Arg Lys Asn Cys Pro Ala Cys Arg Leu Gln Lys Cys Leu Gln Ala
    50                  55                  60

Gly Met
65

<210> SEQ ID NO 12
<211> LENGTH: 66
<212> TYPE: PRT
<213> ORGANISM: Homo sapiens

<400> SEQUENCE: 12

Cys Leu Val Cys Ser Asp Glu Ala Ser Gly Cys His Tyr Gly Val Leu
1               5                   10                  15

Thr Cys Gly Ser Cys Lys Val Phe Phe Lys Arg Ala Val Glu Gly Gln
            20                  25                  30

His Asn Tyr Leu Cys Ala Gly Arg Asn Asp Cys Ile Ile Asp Lys Ile
        35                  40                  45

Arg Arg Lys Asn Cys Pro Ala Cys Arg Tyr Arg Lys Cys Leu Gln Ala
    50                  55                  60

Gly Met
65

<210> SEQ ID NO 13
<211> LENGTH: 66
<212> TYPE: PRT
<213> ORGANISM: Homo sapiens

<400> SEQUENCE: 13

Cys Ala Val Cys Asn Asp Tyr Ala Ser Gly Tyr His Tyr Gly Val Trp
1               5                   10                  15

Ser Cys Glu Gly Cys Lys Ala Phe Phe Lys Arg Ser Ile Gln Gly His
            20                  25                  30

Asn Asp Tyr Met Cys Pro Ala Thr Asn Gln Cys Thr Ile Asp Lys Asn
        35                  40                  45

Arg Arg Lys Ser Cys Gln Ala Cys Arg Leu Arg Lys Cys Tyr Glu Val
    50                  55                  60

Gly Met
65

<210> SEQ ID NO 14
<211> LENGTH: 66
<212> TYPE: PRT
<213> ORGANISM: Gallus gallus

<400> SEQUENCE: 14

Cys Gly Val Cys Gly Asp Arg Ala Thr Gly Phe His Phe Asn Ala Met
1               5                   10                  15

Thr Cys Glu Gly Cys Lys Gly Phe Phe Arg Arg Ser Met Lys Arg Lys
            20                  25                  30

Ala Met Phe Thr Cys Pro Phe Asn Gly Asp Cys Lys Ile Thr Lys Asp
        35                  40                  45

Asn Arg Arg His Cys Gln Ala Cys Arg Leu Lys Arg Cys Val Asp Ile
    50                  55                  60

Gly Met
65

<210> SEQ ID NO 15
<211> LENGTH: 68
<212> TYPE: PRT
<213> ORGANISM: Homo sapiens

<400> SEQUENCE: 15

Cys Val Val Cys Gly Asp Lys Ala Thr Gly Tyr His Tyr Arg Cys Ile
1               5                   10                  15

Thr Cys Glu Gly Cys Lys Gly Phe Phe Arg Arg Thr Ile Gln Lys Asn
            20                  25                  30

Leu His Pro Ser Tyr Ser Cys Lys Tyr Glu Gly Lys Cys Val Ile Asp
        35                  40                  45

Lys Val Thr Arg Asn Gln Cys Gln Glu Cys Arg Phe Lys Lys Cys Ile
    50                  55                  60

Tyr Val Gly Met
65

<210> SEQ ID NO 16
<211> LENGTH: 68
<212> TYPE: PRT
<213> ORGANISM: Avian erythroblastosis virus

<400> SEQUENCE: 16

Cys Val Val Cys Gly Asp Lys Ala Thr Gly Tyr His Tyr Arg Cys Ile
1               5                   10                  15

Thr Cys Glu Gly Cys Lys Ser Phe Phe Arg Arg Thr Ile Gln Lys Asn
            20                  25                  30

Leu His Pro Thr Thr Ser Cys Thr Tyr Asp Gly Cys Cys Val Ile Asp
        35                  40                  45

Lys Ile Thr Arg Asn Gln Cys Gln Leu Cys Arg Phe Lys Lys Cys Ile
    50                  55                  60

```
Ser Val Gly Met
65

<210> SEQ ID NO 17
<211> LENGTH: 66
<212> TYPE: PRT
<213> ORGANISM: Homo sapiens

<400> SEQUENCE: 17

Cys Phe Val Cys Gln Asp Lys Ser Ser Gly Tyr His Tyr Gly Val Ser
1               5                   10                  15

Ala Cys Glu Gly Cys Lys Gly Phe Phe Arg Arg Ser Ile Gln Lys Asn
            20                  25                  30

Met Val Tyr Thr Cys His Arg Asp Lys Asn Cys Ile Ile Asn Lys Val
        35                  40                  45

Thr Arg Asn Arg Cys Gln Tyr Cys Arg Leu Gln Lys Cys Phe Glu Val
    50                  55                  60

Gly Met
65

<210> SEQ ID NO 18
<211> LENGTH: 5082
<212> TYPE: DNA
<213> ORGANISM: Homo sapiens
<220> FEATURE:
<221> NAME/KEY: misc_feature
<222> LOCATION: (360)..(360)
<223> OTHER INFORMATION: "n" denotes any nucleotide
<220> FEATURE:
<221> NAME/KEY: misc_feature
<222> LOCATION: (365)..(365)
<223> OTHER INFORMATION: "n" denotes any nucleotide
<220> FEATURE:
<221> NAME/KEY: misc_feature
<222> LOCATION: (376)..(376)
<223> OTHER INFORMATION: "n" denotes any nucleotide
<220> FEATURE:
<221> NAME/KEY: misc_feature
<222> LOCATION: (385)..(385)
<223> OTHER INFORMATION: "n" denotes any nucleotide
<220> FEATURE:
<221> NAME/KEY: misc_feature
<222> LOCATION: (399)..(399)
<223> OTHER INFORMATION: "n" denotes any nucleotide
<220> FEATURE:
<221> NAME/KEY: misc_feature
<222> LOCATION: (407)..(407)
<223> OTHER INFORMATION: "n" denotes any nucleotide
<220> FEATURE:
<221> NAME/KEY: misc_feature
<222> LOCATION: (417)..(417)
<223> OTHER INFORMATION: "n" denotes any nucleotide
<220> FEATURE:
<221> NAME/KEY: misc_feature
<222> LOCATION: (422)..(422)
<223> OTHER INFORMATION: "n" denotes any nucleotide
<220> FEATURE:
<221> NAME/KEY: misc_feature
<222> LOCATION: (435)..(435)
<223> OTHER INFORMATION: "n" denotes any nucleotide
<220> FEATURE:
<221> NAME/KEY: misc_feature
<222> LOCATION: (439)..(439)
<223> OTHER INFORMATION: "n" denotes any nucleotide
<220> FEATURE:
<221> NAME/KEY: misc_feature
<222> LOCATION: (441)..(441)
<223> OTHER INFORMATION: "n" denotes any nucleotide
<220> FEATURE:
<221> NAME/KEY: misc_feature
<222> LOCATION: (598)..(598)
<223> OTHER INFORMATION: "n" denotes any nucleotide
```

```
<220> FEATURE:
<221> NAME/KEY: misc_feature
<222> LOCATION: (689)..(689)
<223> OTHER INFORMATION: "n" denotes any nucleotide
<220> FEATURE:
<221> NAME/KEY: misc_feature
<222> LOCATION: (714)..(715)
<223> OTHER INFORMATION: "n" denotes any nucleotide
<220> FEATURE:
<221> NAME/KEY: misc_feature
<222> LOCATION: (844)..(844)
<223> OTHER INFORMATION: "n" denotes any nucleotide
<220> FEATURE:
<221> NAME/KEY: misc_feature
<222> LOCATION: (870)..(870)
<223> OTHER INFORMATION: "n" denotes any nucleotide
<220> FEATURE:
<221> NAME/KEY: misc_feature
<222> LOCATION: (918)..(918)
<223> OTHER INFORMATION: "n" denotes any nucleotide
<220> FEATURE:
<221> NAME/KEY: misc_feature
<222> LOCATION: (932)..(932)
<223> OTHER INFORMATION: "n" denotes any nucleotide
<220> FEATURE:
<221> NAME/KEY: misc_feature
<222> LOCATION: (1195)..(1195)
<223> OTHER INFORMATION: "n" denotes any nucleotide
<220> FEATURE:
<221> NAME/KEY: misc_feature
<222> LOCATION: (1198)..(1198)
<223> OTHER INFORMATION: "n" denotes any nucleotide
<220> FEATURE:
<221> NAME/KEY: misc_feature
<222> LOCATION: (1202)..(1202)
<223> OTHER INFORMATION: "n" denotes any nucleotide
<220> FEATURE:
<221> NAME/KEY: misc_feature
<222> LOCATION: (1248)..(1248)
<223> OTHER INFORMATION: "n" denotes any nucleotide
<220> FEATURE:
<221> NAME/KEY: misc_feature
<222> LOCATION: (1322)..(1322)
<223> OTHER INFORMATION: "n" denotes any nucleotide
<220> FEATURE:
<221> NAME/KEY: CDS
<222> LOCATION: (1864)..(4632)

<400> SEQUENCE: 18
gagctctgga caaaattgag cgcctatgtg tacatggcaa gtgtttttag tgtttgtgtg      60
tttacctgct tgtctgggtg attttgcctt tgagagtctg gatgagaaat gcatggttaa     120
aggcaattcc agacaggaag aaaggcagag aagagggtag aaatgacctc tgattcttgg     180
ggctgagggt tcctagagca aatggcacaa tgccacgagg cccgatctat ccctatgacg     240
gaactctaag gtttcagcat cagctatctg ctggcttggt cactggcttg cctcctcagt     300
ttgtaggaga ctctcccact ctcccatctg cgcgctctta tcagtcctga aaagaaccc n   360 tggcnagcca ggagcnaggt attcntatcg tccttttcnt cctcctngcc tcacctngtt     420 gnttttaga ttggncttng naaccaaatt tgtatgctgg cctccaggaa atctggagcc      480
tggcgcctaa accttggttt aggaaagcag gagctattca ggaagcaggg tcctccaggg     540
ctagagctag cctctcctgc cctcgcccac gtgcgccagc acttgtttct ccaaagcnac     600
taggcaggcg ttagcgcgcg gtgagggag gggagaaaag gaaaggggag gggagggaaa      660
aggaggtggg aaggcaagga ggccggccng gtggggcgg gacccgactc gcannaactg      720
ttgcatttgc tctccaccct ccagcgcccc ctccgagatc ccggggagcc agcttgctgg     780
gagagcggga acggtccgga gcaagcccag aggcagagga ggcgacagag ggaaaaaggg     840
cccnagctag ccgctccagt gctgtacagn agccgaagga cgcaccacgc cagccccagc    900
```

```
ccggctccag cgacagcnaa cgcctcttgc angcgttcga agccgccgcc cggagctgcc    960
ctttcctctt cggtgaagtt tttaaaagct gctaaagact cggaggaagc aaggaaagtg   1020
cctggtagga ctgacggctg cctttgtcct cctcctctcc accccgcctc ccccaccct   1080
gccttccccc cctcccccgt cttctctccc gcagctgcct cagtcggcta ctctcagcca   1140
acccccctca ccaccttct ccccaccccgc cccccgccc ccgtcggccc agcgntgnca   1200
gnccgagttt gcagagaggt aactcccttt ggctgcgagc gggcgagnct agctgcacat   1260
tgcaaagaag gctcttagga gcaggcgact ggggagcggc ttcagcactg cagccacgac   1320
cngcctggtt aggctgcacg cggagagaac cctctgtttt cccccactct ctctccacct   1380
cctcctgcct tccccacccc gagtgcggag ccagagatca aaagatgaaa aggcagtcag   1440
gtcttcagta gccaaaaaac aaaacaaaca aaaacaaaaa agccgaaata aagaaaaag    1500
ataataactc agttcttatt tgcacctact tcagtggaca ctgaatttgg aaggtggagg   1560
attttgtttt tttcttttaa gatctgggca tcttttgaat ctaccttca agtattaaga    1620
gacagactgt gagcctagca gggcagatct tgtccaccgt gtgtcttctt ctgcacgaga   1680
ctttgaggct gtcagagcgc tttttgcgtg gttgctcccg caagtttcct tctctggagc   1740
ttcccgcagg tgggcagcta gctgcagcga ctaccgcatc atcacagcct gttgaactct   1800
tctgagcaag agaaggggag gcggggtaag ggaagtaggt ggaagattca gccaagctca   1860
```

| agg atg gaa gtg cag tta ggg ctg gga agg gtc tac cct cgg ccg ccg | 1908 |
| Met Glu Val Gln Leu Gly Leu Gly Arg Val Tyr Pro Arg Pro Pro | |
| 1   5                 10                15 | |

| tcc aag acc tac cga gga gct ttc cag aat ctg ttc cag agc gtg cgc | 1956 |
| Ser Lys Thr Tyr Arg Gly Ala Phe Gln Asn Leu Phe Gln Ser Val Arg | |
| 20                  25                30 | |

| gaa gtg atc cag aac ccg ggc ccc agg cac cca gag gcc gcg agc gca | 2004 |
| Glu Val Ile Gln Asn Pro Gly Pro Arg His Pro Glu Ala Ala Ser Ala | |
| 35              40               45 | |

| gca cct ccc ggc gcc agt ttg ctg ctg ctg cag cag cag cag cag cag | 2052 |
| Ala Pro Pro Gly Ala Ser Leu Leu Leu Leu Gln Gln Gln Gln Gln Gln | |
| 50              55                60 | |

| cag cag cag cag cag cag cag cag cag cag cag cag cag cag cag cag | 2100 |
| Gln Gln Gln Gln Gln Gln Gln Gln Gln Gln Gln Gln Gln Gln Gln Gln | |
| 65              70                75 | |

| cag cag caa gag act agc ccc agg cag cag cag cag cag cag ggt gag | 2148 |
| Gln Gln Gln Glu Thr Ser Pro Arg Gln Gln Gln Gln Gln Gln Gly Glu | |
| 80              85                90               95 | |

| gat ggt tct ccc caa gcc cat cgt aga ggc ccc aca ggc tac ctg gtc | 2196 |
| Asp Gly Ser Pro Gln Ala His Arg Arg Gly Pro Thr Gly Tyr Leu Val | |
| 100             105              110 | |

| ctg gat gag gaa cag caa cct tca cag ccg cag tcg gcc ctg gag tgc | 2244 |
| Leu Asp Glu Glu Gln Gln Pro Ser Gln Pro Gln Ser Ala Leu Glu Cys | |
| 115             120              125 | |

| cac ccc gag aga ggt tgc gtc cca gag cct gga gcc gcc gtg gcc gcc | 2292 |
| His Pro Glu Arg Gly Cys Val Pro Glu Pro Gly Ala Ala Val Ala Ala | |
| 130             135              140 | |

| agc aag ggg ctg ccg cag cag ctg cca gca cct ccg gac gag gat gac | 2340 |
| Ser Lys Gly Leu Pro Gln Gln Leu Pro Ala Pro Pro Asp Glu Asp Asp | |
| 145             150              155 | |

| tca gct gcc cca tcc acg ttg tcc ctg ctg ggc ccc act ttc ccc ggc | 2388 |
| Ser Ala Ala Pro Ser Thr Leu Ser Leu Leu Gly Pro Thr Phe Pro Gly | |
| 160             165              170             175 | |

| tta agc agc tgc tcc gct gac ctt aaa gac atc ctg agc gag gcc agc | 2436 |
| Leu Ser Ser Cys Ser Ala Asp Leu Lys Asp Ile Leu Ser Glu Ala Ser | |

-continued

|  |  |  |  |  |  |  |  |  |  |  |  |  |  |  |  |
|---|---|---|---|---|---|---|---|---|---|---|---|---|---|---|---|
|  |  | 180 |  |  |  |  | 185 |  |  |  |  | 190 |  |  |  |

```
acc atg caa ctc ctt cag caa cag cag cag gaa gca gta tcc gaa ggc    2484
Thr Met Gln Leu Leu Gln Gln Gln Gln Gln Glu Ala Val Ser Glu Gly
            195                 200                 205 agc agc agc ggg aga gcg agg gag gcc tcg ggg gct ccc act tcc tcc    2532
Ser Ser Ser Gly Arg Ala Arg Glu Ala Ser Gly Ala Pro Thr Ser Ser
        210                 215                 220 aag gac aat tac tta ggg ggc act tcg acc att tct gac aac gcc aag    2580
Lys Asp Asn Tyr Leu Gly Gly Thr Ser Thr Ile Ser Asp Asn Ala Lys
    225                 230                 235 gag ttg tgt aag gca gtg tcg gtg tcc atg ggc ctg ggt gtg gag gcg    2628
Glu Leu Cys Lys Ala Val Ser Val Ser Met Gly Leu Gly Val Glu Ala
240                 245                 250                 255 ttg gag cat ctg agt cca ggg gaa cag ctt cgg ggg gat tgc atg tac    2676
Leu Glu His Leu Ser Pro Gly Glu Gln Leu Arg Gly Asp Cys Met Tyr
                260                 265                 270 gcc cca ctt ttg gga gtt cca ccc gct gtg cgt ccc act cct tgt gcc    2724
Ala Pro Leu Leu Gly Val Pro Pro Ala Val Arg Pro Thr Pro Cys Ala
            275                 280                 285 cca ttg gcc gaa tgc aaa ggt tct ctg cta gac gac agc gca ggc aag    2772
Pro Leu Ala Glu Cys Lys Gly Ser Leu Leu Asp Asp Ser Ala Gly Lys
        290                 295                 300 agc act gaa gat act gct gag tat tcc cct ttc aag gga ggt tac acc    2820
Ser Thr Glu Asp Thr Ala Glu Tyr Ser Pro Phe Lys Gly Gly Tyr Thr
    305                 310                 315 aaa ggg cta gaa ggc gag agc cta ggc tgc tct ggc agc gct gca gca    2868
Lys Gly Leu Glu Gly Glu Ser Leu Gly Cys Ser Gly Ser Ala Ala Ala
320                 325                 330                 335 ggg agc tcc ggg aca ctt gaa ctg ccg tct acc ctg tct ctc tac aag    2916
Gly Ser Ser Gly Thr Leu Glu Leu Pro Ser Thr Leu Ser Leu Tyr Lys
                340                 345                 350 tcc gga gca ctg gac gag gca gct gcg tac cag agt cgc gac tac tac    2964
Ser Gly Ala Leu Asp Glu Ala Ala Ala Tyr Gln Ser Arg Asp Tyr Tyr
            355                 360                 365 aac ttt cca ctg gct ctg gcc gga ccg ccg ccc cct ccg ccg cct ccc    3012
Asn Phe Pro Leu Ala Leu Ala Gly Pro Pro Pro Pro Pro Pro Pro Pro
        370                 375                 380 cat ccc cac gct cgc atc aag ctg gag aac ccg ctg gac tac ggc agc    3060
His Pro His Ala Arg Ile Lys Leu Glu Asn Pro Leu Asp Tyr Gly Ser
    385                 390                 395 gcc tgg gcg gct gcg gcg gcg cag tgc cgc tat ggg gac ctg gcg agc    3108
Ala Trp Ala Ala Ala Ala Ala Gln Cys Arg Tyr Gly Asp Leu Ala Ser
400                 405                 410                 415 ctg cat ggc gcg ggt gca gcg gga ccc ggt tct ggg tca ccc tca gcc    3156
Leu His Gly Ala Gly Ala Ala Gly Pro Gly Ser Gly Ser Pro Ser Ala
                420                 425                 430 gcc gct tcc tca tcc tgg cac act ctc ttc aca gcc gaa gaa ggc cag    3204
Ala Ala Ser Ser Ser Trp His Thr Leu Phe Thr Ala Glu Glu Gly Gln
            435                 440                 445 ttg tat gga ccg tgt ggt ggt ggg ggt ggt ggc ggc ggc ggc ggc        3252
Leu Tyr Gly Pro Cys Gly Gly Gly Gly Gly Gly Gly Gly Gly Gly
        450                 455                 460 ggc ggc ggc ggc ggc ggc ggc ggc ggc ggc ggc ggc gag gcg gga        3300
Gly Gly Gly Gly Gly Gly Gly Gly Gly Gly Gly Gly Glu Ala Gly
    465                 470                 475 gct gta gcc ccc tac ggc tac act cgg ccc cct cag ggg ctg gcg ggc    3348
Ala Val Ala Pro Tyr Gly Tyr Thr Arg Pro Pro Gln Gly Leu Ala Gly
480                 485                 490                 495 cag gaa agc gac ttc acc gca cct gat gtg tgg tac cct ggc ggc atg    3396
Gln Glu Ser Asp Phe Thr Ala Pro Asp Val Trp Tyr Pro Gly Gly Met
```

```
                Gln Glu Ser Asp Phe Thr Ala Pro Asp Val Trp Tyr Pro Gly Gly Met
                                500                 505                 510 gtg agc aga gtg ccc tat ccc agt ccc act tgt gtc aaa agc gaa atg          3444
Val Ser Arg Val Pro Tyr Pro Ser Pro Thr Cys Val Lys Ser Glu Met
            515                 520                 525 ggc ccc tgg atg gat agc tac tcc gga cct tac ggg gac atg cgt ttg          3492
Gly Pro Trp Met Asp Ser Tyr Ser Gly Pro Tyr Gly Asp Met Arg Leu
        530                 535                 540 gag act gcc agg gac cat gtt ttg ccc att gac tat tac ttt cca ccc          3540
Glu Thr Ala Arg Asp His Val Leu Pro Ile Asp Tyr Tyr Phe Pro Pro
    545                 550                 555 cag aag acc tgc ctg atc tgt gga gat gaa gct tct ggg tgt cac tat          3588
Gln Lys Thr Cys Leu Ile Cys Gly Asp Glu Ala Ser Gly Cys His Tyr
560                 565                 570                 575 gga gct ctc aca tgt gga agc tgc aag gtc ttc ttc aaa aga gcc gct          3636
Gly Ala Leu Thr Cys Gly Ser Cys Lys Val Phe Phe Lys Arg Ala Ala
            580                 585                 590 gaa ggg aaa cag aag tac ctg tgc gcc agc aga aat gat tgc act att          3684
Glu Gly Lys Gln Lys Tyr Leu Cys Ala Ser Arg Asn Asp Cys Thr Ile
        595                 600                 605 gat aaa ttc cga agg aaa aat tgt cca tct tgt cgt ctt cgg aaa tgt          3732
Asp Lys Phe Arg Arg Lys Asn Cys Pro Ser Cys Arg Leu Arg Lys Cys
    610                 615                 620 tat gaa gca ggg atg act ctg gga gcc cgg aag ctg aag aaa ctt ggt          3780
Tyr Glu Ala Gly Met Thr Leu Gly Ala Arg Lys Leu Lys Lys Leu Gly
625                 630                 635 aat ctg aaa cta cag gag gaa gga gag gct tcc agc acc acc agc ccc          3828
Asn Leu Lys Leu Gln Glu Glu Gly Glu Ala Ser Ser Thr Thr Ser Pro
640                 645                 650                 655 act gag gag aca acc cag aag ctg aca gtg tca cac att gaa ggc tat          3876
Thr Glu Glu Thr Thr Gln Lys Leu Thr Val Ser His Ile Glu Gly Tyr
            660                 665                 670 gaa tgt cag ccc atc ttt ctg aat gtc ctg gaa gcc att gag cca ggt          3924
Glu Cys Gln Pro Ile Phe Leu Asn Val Leu Glu Ala Ile Glu Pro Gly
        675                 680                 685 gta gtg tgt gct gga cac gac aac aac cag ccc gac tcc ttt gca gcc          3972
Val Val Cys Ala Gly His Asp Asn Asn Gln Pro Asp Ser Phe Ala Ala
    690                 695                 700 ttg ctc tct agc ctc aat gaa ctg gga gag aga cag ctt gta cac gtg          4020
Leu Leu Ser Ser Leu Asn Glu Leu Gly Glu Arg Gln Leu Val His Val
705                 710                 715 gtc aag tgg gcc aag gcc ttg cct ggc ttc cgc aac tta cac gtg gac          4068
Val Lys Trp Ala Lys Ala Leu Pro Gly Phe Arg Asn Leu His Val Asp
720                 725                 730                 735 gac cag atg gct gtc att cag tac tcc tgg atg ggg ctc atg gtg ttt          4116
Asp Gln Met Ala Val Ile Gln Tyr Ser Trp Met Gly Leu Met Val Phe
            740                 745                 750 gcc atg ggc tgg cga tcc ttc acc aat gtc aac tcc agg atg ctc tac          4164
Ala Met Gly Trp Arg Ser Phe Thr Asn Val Asn Ser Arg Met Leu Tyr
        755                 760                 765 ttc gcc cct gat ctg gtt ttc aat gag tac cgc atg cac aag tcc cgg          4212
Phe Ala Pro Asp Leu Val Phe Asn Glu Tyr Arg Met His Lys Ser Arg
    770                 775                 780 atg tac agc cag tgt gtc cga atg agg cac ctc tct caa gag ttt gga          4260
Met Tyr Ser Gln Cys Val Arg Met Arg His Leu Ser Gln Glu Phe Gly
785                 790                 795 tgg ctc caa atc acc ccc cag gaa ttc ctg tgc atg aaa gca ctg cta          4308
Trp Leu Gln Ile Thr Pro Gln Glu Phe Leu Cys Met Lys Ala Leu Leu
800                 805                 810                 815
```

-continued

```
ctc ttc agc att att cca gtg gat ggg ctg aaa aat caa aaa ttc ttt    4356
Leu Phe Ser Ile Ile Pro Val Asp Gly Leu Lys Asn Gln Lys Phe Phe
            820                 825                 830 gat gaa ctt cga atg aac tac atc aag gaa ctc gat cgt atc att gca    4404
Asp Glu Leu Arg Met Asn Tyr Ile Lys Glu Leu Asp Arg Ile Ile Ala
        835                 840                 845 tgc aaa aga aaa aat ccc aca tcc tgc tca aga cgc ttc tac cag ctc    4452
Cys Lys Arg Lys Asn Pro Thr Ser Cys Ser Arg Arg Phe Tyr Gln Leu
    850                 855                 860 acc aag ctc ctg gac tcc gtg cag cct att gcg aga gag ctg cat cag    4500
Thr Lys Leu Leu Asp Ser Val Gln Pro Ile Ala Arg Glu Leu His Gln
865                 870                 875 ttc act ttt gac ctg cta atc aag tca cac atg gtg agc gtg gac ttt    4548
Phe Thr Phe Asp Leu Leu Ile Lys Ser His Met Val Ser Val Asp Phe
880                 885                 890                 895 ccg gaa atg atg gca gag atc atc tct gtg caa gtg ccc aag atc ctt    4596
Pro Glu Met Met Ala Glu Ile Ile Ser Val Gln Val Pro Lys Ile Leu
                900                 905                 910 tct ggg aaa gtc aag ccc atc tat ttc cac acc cag tgaagcattg         4642
Ser Gly Lys Val Lys Pro Ile Tyr Phe His Thr Gln
            915                 920 gaaaccctat ttccccaccc cagctcatgc cccctttcag atgtcttctg cctgttataa  4702
ctctgcacta ctcctctgca gtgccttggg gaatttcctc tattgatgta cagtctgtca  4762
tgaacatgtt cctgaattct atttgctggg ctttttttt ctctttctct cctttctttt   4822
tcttcttccc tccctatcta accctcccat ggcaccttca gactttgctt cccattgtgg  4882
ctcctatctg tgttttgaat ggtgttgtat gcctttaaat ctgtgatgat cctcatatgg  4942
cccagtgtca agttgtgctt gtttacagca ctactctgtg ccagccacac aaacgtttac  5002
ttatcttatg ccacgggaag tttagagagc taagattatc tggggaaatc aaaacaaaaa  5062
acaagcaaac aaaaaaaaaa                                              5082
```

<210> SEQ ID NO 19
<211> LENGTH: 923
<212> TYPE: PRT
<213> ORGANISM: Homo sapiens

<400> SEQUENCE: 19

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Glu Thr Ser Pro Arg Gln Gln Gln Gln Gln Gly Glu Asp
            85                  90                  95

Gly Ser Pro Gln Ala His Arg Arg Gly Pro Thr Gly Tyr Leu Val Leu
            100                 105                 110

Asp Glu Glu Gln Gln Pro Ser Gln Pro Gln Ser Ala Leu Glu Cys His
        115                 120                 125

Pro Glu Arg Gly Cys Val Pro Glu Pro Gly Ala Ala Val Ala Ala Ser
    130                 135                 140
```

```
                                    -continued
Lys Gly Leu Pro Gln Gln Leu Pro Ala Pro Pro Asp Glu Asp Ser
145                 150                 155                 160

Ala Ala Pro Ser Thr Leu Ser Leu Leu Gly Pro Thr Phe Pro Gly Leu
                165                 170                 175

Ser Ser Cys Ser Ala Asp Leu Lys Asp Ile Leu Ser Glu Ala Ser Thr
            180                 185                 190

Met Gln Leu Leu Gln Gln Gln Gln Glu Ala Val Ser Glu Gly Ser
        195                 200                 205

Ser Ser Gly Arg Ala Arg Glu Ala Ser Gly Ala Pro Thr Ser Ser Lys
    210                 215                 220

Asp Asn Tyr Leu Gly Gly Thr Ser Thr Ile Ser Asp Asn Ala Lys Glu
225                 230                 235                 240

Leu Cys Lys Ala Val Ser Val Ser Met Gly Leu Gly Val Glu Ala Leu
                245                 250                 255

Glu His Leu Ser Pro Gly Glu Gln Leu Arg Gly Asp Cys Met Tyr Ala
            260                 265                 270

Pro Leu Leu Gly Val Pro Pro Ala Val Arg Pro Thr Pro Cys Ala Pro
        275                 280                 285

Leu Ala Glu Cys Lys Gly Ser Leu Leu Asp Asp Ser Ala Gly Lys Ser
    290                 295                 300

Thr Glu Asp Thr Ala Glu Tyr Ser Pro Phe Lys Gly Gly Tyr Thr Lys
305                 310                 315                 320

Gly Leu Glu Gly Glu Ser Leu Gly Cys Ser Gly Ser Ala Ala Ala Gly
                325                 330                 335

Ser Ser Gly Thr Leu Glu Leu Pro Ser Thr Leu Ser Leu Tyr Lys Ser
            340                 345                 350

Gly Ala Leu Asp Glu Ala Ala Tyr Gln Ser Arg Asp Tyr Tyr Asn
        355                 360                 365

Phe Pro Leu Ala Leu Ala Gly Pro Pro Pro Pro Pro Pro Pro His
370                 375                 380

Pro His Ala Arg Ile Lys Leu Glu Asn Pro Leu Asp Tyr Gly Ser Ala
385                 390                 395                 400

Trp Ala Ala Ala Ala Gln Cys Arg Tyr Gly Asp Leu Ala Ser Leu
                405                 410                 415

His Gly Ala Gly Ala Ala Gly Pro Gly Ser Gly Ser Pro Ser Ala Ala
            420                 425                 430

Ala Ser Ser Ser Trp His Thr Leu Phe Thr Ala Glu Glu Gly Gln Leu
        435                 440                 445

Tyr Gly Pro Cys Gly Gly Gly Gly Gly Gly Gly Gly Gly Gly Gly
    450                 455                 460

Gly Gly Gly Gly Gly Gly Gly Gly Gly Gly Glu Ala Gly Ala
465                 470                 475                 480

Val Ala Pro Tyr Gly Tyr Thr Arg Pro Pro Gln Gly Leu Ala Gly Gln
                485                 490                 495

Glu Ser Asp Phe Thr Ala Pro Asp Val Trp Tyr Pro Gly Gly Met Val
            500                 505                 510

Ser Arg Val Pro Tyr Pro Ser Pro Thr Cys Val Lys Ser Glu Met Gly
        515                 520                 525

Pro Trp Met Asp Ser Tyr Ser Gly Pro Tyr Gly Asp Met Arg Leu Glu
    530                 535                 540

Thr Ala Arg Asp His Val Leu Pro Ile Asp Tyr Tyr Phe Pro Pro Gln
545                 550                 555                 560

Lys Thr Cys Leu Ile Cys Gly Asp Glu Ala Ser Gly Cys His Tyr Gly
```

```
                          565                 570                 575
Ala Leu Thr Cys Gly Ser Cys Lys Val Phe Lys Arg Ala Ala Glu
            580                 585                 590
Gly Lys Gln Lys Tyr Leu Cys Ala Ser Arg Asn Asp Cys Thr Ile Asp
            595                 600                 605
Lys Phe Arg Arg Lys Asn Cys Pro Ser Cys Arg Leu Arg Lys Cys Tyr
610                 615                 620
Glu Ala Gly Met Thr Leu Gly Ala Arg Lys Leu Lys Lys Leu Gly Asn
625                 630                 635                 640
Leu Lys Leu Gln Glu Glu Gly Glu Ala Ser Ser Thr Thr Ser Pro Thr
            645                 650                 655
Glu Glu Thr Thr Gln Lys Leu Thr Val Ser His Ile Glu Gly Tyr Glu
            660                 665                 670
Cys Gln Pro Ile Phe Leu Asn Val Leu Glu Ala Ile Glu Pro Gly Val
            675                 680                 685
Val Cys Ala Gly His Asp Asn Asn Gln Pro Asp Ser Phe Ala Ala Leu
            690                 695                 700
Leu Ser Ser Leu Asn Glu Leu Gly Glu Arg Gln Leu Val His Val Val
705                 710                 715                 720
Lys Trp Ala Lys Ala Leu Pro Gly Phe Arg Asn Leu His Val Asp Asp
                        725                 730                 735
Gln Met Ala Val Ile Gln Tyr Ser Trp Met Gly Leu Met Val Phe Ala
                        740                 745                 750
Met Gly Trp Arg Ser Phe Thr Asn Val Asn Ser Arg Met Leu Tyr Phe
            755                 760                 765
Ala Pro Asp Leu Val Phe Asn Glu Tyr Arg Met His Lys Ser Arg Met
770                 775                 780
Tyr Ser Gln Cys Val Arg Met Arg His Leu Ser Gln Glu Phe Gly Trp
785                 790                 795                 800
Leu Gln Ile Thr Pro Gln Glu Phe Leu Cys Met Lys Ala Leu Leu Leu
                        805                 810                 815
Phe Ser Ile Ile Pro Val Asp Gly Leu Lys Asn Gln Lys Phe Phe Asp
                        820                 825                 830
Glu Leu Arg Met Asn Tyr Ile Lys Glu Leu Asp Arg Ile Ile Ala Cys
            835                 840                 845
Lys Arg Lys Asn Pro Thr Ser Cys Ser Arg Arg Phe Tyr Gln Leu Thr
850                 855                 860
Lys Leu Leu Asp Ser Val Gln Pro Ile Ala Arg Glu Leu His Gln Phe
865                 870                 875                 880
Thr Phe Asp Leu Leu Ile Lys Ser His Met Val Ser Val Asp Phe Pro
                        885                 890                 895
Glu Met Met Ala Glu Ile Ile Ser Val Gln Val Pro Lys Ile Leu Ser
                        900                 905                 910
Gly Lys Val Lys Pro Ile Tyr Phe His Thr Gln
            915                 920

<210> SEQ ID NO 20
<211> LENGTH: 4289
<212> TYPE: DNA
<213> ORGANISM: Rattus rattus
<220> FEATURE:
<221> NAME/KEY: CDS
<222> LOCATION: (1123)..(3828)

<400> SEQUENCE: 20
```

-continued

```
aattcgggaa ggatcgagca aaccaggaaa gtaaggatgg agatcctagg agagtgtcca      60
tgcctcgaaa ggagcccacc aaagatgaac tgttgcattt gctttccacc tcccagcgcc     120
ccctcggaga tccctaggag ccagcctgct gggagaacca gagggtccgg agcaaacctg     180
gaggctgaga gggcatcaga ggggaaaaga ctgagttagc cactccagtg ccatacagaa     240
gcttaaggga cataccacgc cagccccagc cagcgacag ccaacgcctg ttgcagagcg      300
gcggcttcga agccgccgcc cagaagctgc cctttcctct tcggtgaagt ttctaaaagc     360
tgcgggagac tcggaggaag cgaagaaagt gtccggtagg actacgactg cctttgtcct     420
cctccctcct accccctaccc ctcctgggtc ccctctccct gagcggacta ggcaggcttc    480
ctggccagcc ctctccccta caccaccagc tctgccagcc agtttgcaca gaggtaactc     540
cctttggctg aaagcagacg agcttgttgc ccattggaag ggaggctttt gggagcccag     600
agactgagga gcaacagcac gctggagagt ccctgattcc aggttctccc ccctgcacct    660
cctactgccc gcccctcacc ctgtgtgtgc agctagaatt gaaagatgaa aagacagtt     720 ggggcttcag tagtcgaaag caaaacaaaa gcaaaagaa acaaaaaga aaatagccca      780 gttcttattt gcacctgctt cagtggacat tgactttgga aggcagagaa ttttccttcc    840
ccccagtcaa gctttgagca tcttttaatc tgttcttcaa gtatttaggg acaaactgtg    900
aaactagcag gcagatcct gtctagcgcg tgccttcctt tacaggagac tttgaggcta    960
tctgggcgct ccccccctc cctgcaagtt ttcttccctg gagcttcccg caggtgggca    1020
gctagctgca gatactacat catcagtcag tagaactctt cagagcaaga gacgaggagg   1080
caggataagg gaattcggtg gaagctagag acaagctaaa gg atg gag gtg cag       1134
                                              Met Glu Val Gln
                                                1 tta ggg ctg gga agg gtc tac cca cgg ccc ccg tcc aag acc tat cga       1182
Leu Gly Leu Gly Arg Val Tyr Pro Arg Pro Pro Ser Lys Thr Tyr Arg
 5              10                  15                  20 gga gcg ttc cag aat ctg ttc cag agc gtg cgc gaa gcg atc cag aac       1230
Gly Ala Phe Gln Asn Leu Phe Gln Ser Val Arg Glu Ala Ile Gln Asn
             25                  30                  35 ccg ggc ccc agg cac cct gag gcc gct agc ata gca cct ccc ggt gcc       1278
Pro Gly Pro Arg His Pro Glu Ala Ala Ser Ile Ala Pro Pro Gly Ala
         40                  45                  50 tgt tta cag cag cgg cag gag act agc ccc cgg cgg cgg cgg cgg cag       1326
Cys Leu Gln Gln Arg Gln Glu Thr Ser Pro Arg Arg Arg Arg Arg Gln
     55                  60                  65 cag cac cct gag gat ggc tct cct caa gcc cac atc aga ggc acc aca       1374
Gln His Pro Glu Asp Gly Ser Pro Gln Ala His Ile Arg Gly Thr Thr
 70                  75                  80 ggc tac ctg gcc ctg gag gag gaa cag cag cct tca cag cag cag tca       1422
Gly Tyr Leu Ala Leu Glu Glu Glu Gln Gln Pro Ser Gln Gln Gln Ser
85                  90                  95                 100 gcc tcc gag ggc cac cct gag agc ggc tgc ctc ccg gag cct gga gct       1470
Ala Ser Glu Gly His Pro Glu Ser Gly Cys Leu Pro Glu Pro Gly Ala
             105                 110                 115 gcc acg gct cct ggc aag ggg ctg ccg cag cag cca cca gct cct cca       1518
Ala Thr Ala Pro Gly Lys Gly Leu Pro Gln Gln Pro Pro Ala Pro Pro
         120                 125                 130 gat cag gat gac tca gct gcc cca tcc acg ttg tcc cta ctg ggc ccc       1566
Asp Gln Asp Asp Ser Ala Ala Pro Ser Thr Leu Ser Leu Leu Gly Pro
     135                 140                 145 act ttc cca ggc tta agc agc tgc tcc gca gac att aaa gac atc ctg       1614
Thr Phe Pro Gly Leu Ser Ser Cys Ser Ala Asp Ile Lys Asp Ile Leu
 150                 155                 160
```

-continued

| | |
|---|---|
| agc gag gcc ggc acc atg caa ctt ctt cag cag cag caa cag caa<br>Ser Glu Ala Gly Thr Met Gln Leu Leu Gln Gln Gln Gln Gln Gln<br>165                    170                    175                  180 | 1662 |
| cag cag cag cag cag cag cag cag cag cag caa cag cag cag gag<br>Gln Gln Gln Gln Gln Gln Gln Gln Gln Gln Gln Gln Gln Gln Glu<br>                    185                    190                    195 | 1710 |
| gta ata tcc gaa ggc agc agc gtg aga gca agg gag gcc act ggg<br>Val Ile Ser Glu Gly Ser Ser Val Arg Ala Arg Glu Ala Thr Gly<br>          200                    205                    210 | 1758 |
| gct ccc tct tcc tcc aag gat agt tac cta ggg ggc aat tcg acc ata<br>Ala Pro Ser Ser Ser Lys Asp Ser Tyr Leu Gly Gly Asn Ser Thr Ile<br>              215                    220                    225 | 1806 |
| tct gac agt gcc aag gag ttg tgt aaa gca gtg tct gtg tcc atg ggg<br>Ser Asp Ser Ala Lys Glu Leu Cys Lys Ala Val Ser Val Ser Met Gly<br>230                    235                    240 | 1854 |
| ttg ggt gtg gaa gca ctg gaa cat ctg agt cca ggg gag cag ctt cgg<br>Leu Gly Val Glu Ala Leu Glu His Leu Ser Pro Gly Glu Gln Leu Arg<br>245                    250                    255                    260 | 1902 |
| ggc gac tgc atg tac gcg tcg ctc ctg gga ggt cca ccc gcc gtg cgt<br>Gly Asp Cys Met Tyr Ala Ser Leu Leu Gly Gly Pro Pro Ala Val Arg<br>                    265                    270                    275 | 1950 |
| ccc act cct tgt gcg cct ctg gcc gaa tgc aaa ggt ctt tcc ctg gac<br>Pro Thr Pro Cys Ala Pro Leu Ala Glu Cys Lys Gly Leu Ser Leu Asp<br>              280                    285                    290 | 1998 |
| gaa ggc ccg ggc aaa ggc act gaa gag act gct gag tat tcc tct ttc<br>Glu Gly Pro Gly Lys Gly Thr Glu Glu Thr Ala Glu Tyr Ser Ser Phe<br>295                    300                    305 | 2046 |
| aag gga ggt tac gcc aaa ggg ttg gaa ggt gag agt ctg ggc tgc tct<br>Lys Gly Gly Tyr Ala Lys Gly Leu Glu Gly Glu Ser Leu Gly Cys Ser<br>          310                    315                    320 | 2094 |
| ggc agt agt gaa gca ggt agc tct ggg aca ctt gag atc ccg tcc tca<br>Gly Ser Ser Glu Ala Gly Ser Ser Gly Thr Leu Glu Ile Pro Ser Ser<br>325                    330                    335                    340 | 2142 |
| ctg tct ctg tat aag tct gga gca gta gac gag gca gca gca tac cag<br>Leu Ser Leu Tyr Lys Ser Gly Ala Val Asp Glu Ala Ala Ala Tyr Gln<br>                    345                    350                    355 | 2190 |
| aat cgc gac tac tac aac ttt ccg ctc gct ctg tcc ggg ccg ccg cac<br>Asn Arg Asp Tyr Tyr Asn Phe Pro Leu Ala Leu Ser Gly Pro Pro His<br>              360                    365                    370 | 2238 |
| ccc ccg ccc cct acc cat cca cac gcc cgc atc aag ctg gag aac ccg<br>Pro Pro Pro Pro Thr His Pro His Ala Arg Ile Lys Leu Glu Asn Pro<br>375                    380                    385 | 2286 |
| tcg gac tac ggc agc gcc tgg gct gcg gcg gca gcg caa tgc cgc tat<br>Ser Asp Tyr Gly Ser Ala Trp Ala Ala Ala Ala Gln Cys Arg Tyr<br>390                    395                    400 | 2334 |
| ggg gac ttg gct agc cta cat gga ggg agt gta gcc gga ccc agc act<br>Gly Asp Leu Ala Ser Leu His Gly Gly Ser Val Ala Gly Pro Ser Thr<br>405                    410                    415                    420 | 2382 |
| gga tcg ccc cca gcc acc gcc tct tct tcc tgg cat act ctc ttc aca<br>Gly Ser Pro Pro Ala Thr Ala Ser Ser Ser Trp His Thr Leu Phe Thr<br>                    425                    430                    435 | 2430 |
| gct gaa gaa ggc caa tta tat ggg cca gga ggc ggg ggc ggc agc agt<br>Ala Glu Glu Gly Gln Leu Tyr Gly Pro Gly Gly Gly Gly Gly Ser Ser<br>              440                    445                    450 | 2478 |
| agc cca agc gat gct ggg cct gta gcc ccc tat ggc tac act cgg ccc<br>Ser Pro Ser Asp Ala Gly Pro Val Ala Pro Tyr Gly Tyr Thr Arg Pro<br>          455                    460                    465 | 2526 |
| cct cag ggg ctg gca agc cag gag ggt gac ttc tct gcc tct gaa gtg<br>Pro Gln Gly Leu Ala Ser Gln Glu Gly Asp Phe Ser Ala Ser Glu Val | 2574 |

-continued

```
              470                     475                     480
tgg tat cct ggt gga gtt gtg aac aga gtc ccc tat ccc agt ccc agt       2622
Trp Tyr Pro Gly Gly Val Val Asn Arg Val Pro Tyr Pro Ser Pro Ser
485                     490                     495                 500 tgt gtt aaa agt gaa atg gga cct tgg atg gag aac tac tcc gga cct       2670
Cys Val Lys Ser Glu Met Gly Pro Trp Met Glu Asn Tyr Ser Gly Pro
                    505                     510                 515 tat ggg gac atg cgt ttg gac agt acc agg gac cac gtt tta ccc atc       2718
Tyr Gly Asp Met Arg Leu Asp Ser Thr Arg Asp His Val Leu Pro Ile
                520                     525                 530 gac tat tac ttc cca ccc cag aag acc tgc ctg atc tgt gga gat gaa       2766
Asp Tyr Tyr Phe Pro Pro Gln Lys Thr Cys Leu Ile Cys Gly Asp Glu
            535                     540                 545 gct tct ggt tgt cac tac gga gct ctc act tgt ggc agc tgc aag gtc       2814
Ala Ser Gly Cys His Tyr Gly Ala Leu Thr Cys Gly Ser Cys Lys Val
550                     555                     560 ttc ttc aaa aga gct gcg gaa ggg aaa cag aag tat cta tgt gcc agc       2862
Phe Phe Lys Arg Ala Ala Glu Gly Lys Gln Lys Tyr Leu Cys Ala Ser
565                     570                     575             580 aga aat gat tgc acc att gat aaa ttt cgg agg aaa aat tgt cca tcg       2910
Arg Asn Asp Cys Thr Ile Asp Lys Phe Arg Arg Lys Asn Cys Pro Ser
                    585                     590                 595 tgt cgt ctc cgg aaa tgt tat gaa gca ggg atg act ctg gga gct cgt       2958
Cys Arg Leu Arg Lys Cys Tyr Glu Ala Gly Met Thr Leu Gly Ala Arg
                600                     605                 610 aag ctg aag aaa ctt gga aat ctc aaa cta cag gaa gaa gga gaa aac       3006
Lys Leu Lys Lys Leu Gly Asn Leu Lys Leu Gln Glu Glu Gly Glu Asn
            615                     620                 625 tcc agt gct ggt agc ccc act gag gac cca tcc cag aag atg act gta       3054
Ser Ser Ala Gly Ser Pro Thr Glu Asp Pro Ser Gln Lys Met Thr Val
630                     635                     640 tca cac att gaa ggc tat gaa tgt caa cct atc ttt ctt aat gtc ctg       3102
Ser His Ile Glu Gly Tyr Glu Cys Gln Pro Ile Phe Leu Asn Val Leu
645                     650                     655             660 gaa gcc att gag cca gga gtg gtg tgt gcc gga cat gac aac aac cag       3150
Glu Ala Ile Glu Pro Gly Val Val Cys Ala Gly His Asp Asn Asn Gln
                    665                     670                 675 cct gat tcc ttt gct gcc ttg tta tct agt ctc aac gag ctt ggc gag       3198
Pro Asp Ser Phe Ala Ala Leu Leu Ser Ser Leu Asn Glu Leu Gly Glu
                680                     685                 690 aga cag ctt gta cat gtg gtc aag tgg gcc aag gcc ttg cct ggc ttc       3246
Arg Gln Leu Val His Val Val Lys Trp Ala Lys Ala Leu Pro Gly Phe
            695                     700                 705 cgc aac ttg cat gtg gat gac cag atg gca gtc att cag tat tcc tgg       3294
Arg Asn Leu His Val Asp Asp Gln Met Ala Val Ile Gln Tyr Ser Trp
710                     715                     720 atg gga ctg atg gta ttt gcc atg ggt tgg cgg tcc ttc act aat gtc       3342
Met Gly Leu Met Val Phe Ala Met Gly Trp Arg Ser Phe Thr Asn Val
725                     730                     735             740 aac tct agg atg ctc tac ttt gca cct gac ctg gtt ttc aat gag tat       3390
Asn Ser Arg Met Leu Tyr Phe Ala Pro Asp Leu Val Phe Asn Glu Tyr
                    745                     750                 755 cgc atg cac aag tct cga atg tac agc cag tgc gtg agg atg agg cac       3438
Arg Met His Lys Ser Arg Met Tyr Ser Gln Cys Val Arg Met Arg His
                760                     765                 770 ctt tct caa gag ttt gga tgg ctc cag ata acc ccc cag gaa ttc ctg       3486
Leu Ser Gln Glu Phe Gly Trp Leu Gln Ile Thr Pro Gln Glu Phe Leu
            775                     780                 785 tgc atg aaa gca ctg cta ctc ttc agc att att cca gtg gat ggg ctg       3534
```

```
Cys Met Lys Ala Leu Leu Leu Phe Ser Ile Ile Pro Val Asp Gly Leu
        790                 795                 800 aaa aat caa aaa ttc ttt gat gaa ctt cga atg aac tac atc aag gaa    3582
Lys Asn Gln Lys Phe Phe Asp Glu Leu Arg Met Asn Tyr Ile Lys Glu
805                 810                 815                 820 ctt gat cgc atc att gca tgc aaa aga aaa aat ccc aca tcc tgc tca    3630
Leu Asp Arg Ile Ile Ala Cys Lys Arg Lys Asn Pro Thr Ser Cys Ser
                825                 830                 835 agg cgc ttc tac cag ctc acc aag ctc ctg gat tct gtg cag cct att    3678
Arg Arg Phe Tyr Gln Leu Thr Lys Leu Leu Asp Ser Val Gln Pro Ile
            840                 845                 850 gca aga gag ctg cat caa ttc act ttt gac ctg cta atc aag tcc cat    3726
Ala Arg Glu Leu His Gln Phe Thr Phe Asp Leu Leu Ile Lys Ser His
        855                 860                 865 atg gtg agc gtg gac ttt cct gaa atg atg gca gag atc atc tct gtg    3774
Met Val Ser Val Asp Phe Pro Glu Met Met Ala Glu Ile Ile Ser Val
        870                 875                 880 caa gtg ccc aag atc ctt tct ggg aaa gtc aag ccc atc tat ttc cac    3822
Gln Val Pro Lys Ile Leu Ser Gly Lys Val Lys Pro Ile Tyr Phe His
885                 890                 895                 900 aca cag tgaagatttg aacctaata cccaaaccca cctgttccct tttcagatgt      3878
Thr Gln cttctgcctg ttataaact ctgcactact tctctggcat gggccttggg ggaaattcct   3938
ctactgatgt acagtctgtc atgaacatgt tccccaagtt ctatttcctg gcttttcct   3998 tctttctttt tcttcttctc tgcctctttt accctcccat ggcacatttt gaatccgctg   4058
cgtgttgtgg ctcctgcctg tgttttgagt tttgttgtat ttcttcaagt ctgtgatgat   4118
cttcttgtgg cccagtgtca actgtgcttg tttatagcac tgtgctgtgt gccaaccaag   4178
caaatgttta ctcaccttat gccatggcaa gtttagagag ctataagtat cttgggaaga   4238
aacaaacaga gagagtaaaa aaccaaaaaa aaaaaaaaa aaaccgaatt c              4289

<210> SEQ ID NO 21
<211> LENGTH: 902
<212> TYPE: PRT
<213> ORGANISM: Rattus rattus

<400> SEQUENCE: 21

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Ser Ile Ala
        35                  40                  45

Pro Pro Gly Ala Cys Leu Gln Gln Arg Gln Glu Thr Ser Pro Arg Arg
    50                  55                  60

Arg Arg Arg Gln Gln His Pro Glu Asp Gly Ser Pro Gln Ala His Ile
65                  70                  75                  80

Arg Gly Thr Thr Gly Tyr Leu Ala Leu Glu Glu Glu Gln Gln Pro Ser
                85                  90                  95

Gln Gln Gln Ser Ala Ser Glu Gly His Pro Glu Ser Gly Cys Leu Pro
            100                 105                 110

Glu Pro Gly Ala Ala Thr Ala Pro Gly Lys Gly Leu Pro Gln Gln Pro
        115                 120                 125

Pro Ala Pro Pro Asp Gln Asp Asp Ser Ala Ala Pro Ser Thr Leu Ser
    130                 135                 140
```

```
Leu Leu Gly Pro Thr Phe Pro Gly Leu Ser Ser Cys Ser Ala Asp Ile
145                 150                 155                 160

Lys Asp Ile Leu Ser Glu Ala Gly Thr Met Gln Leu Gln Gln Gln
                165                 170                 175

Gln Gln Gln Gln Gln Gln Gln Gln Gln Gln Gln Gln Gln Gln Gln
            180                 185                 190

Gln Gln Gln Glu Val Ile Ser Glu Gly Ser Ser Val Arg Ala Arg
        195                 200                 205

Glu Ala Thr Gly Ala Pro Ser Ser Lys Asp Ser Tyr Leu Gly Gly
    210                 215                 220

Asn Ser Thr Ile Ser Asp Ser Ala Lys Glu Leu Cys Lys Ala Val Ser
225                 230                 235                 240

Val Ser Met Gly Leu Gly Val Glu Ala Leu Glu His Leu Ser Pro Gly
                245                 250                 255

Glu Gln Leu Arg Gly Asp Cys Met Tyr Ala Ser Leu Leu Gly Gly Pro
                260                 265                 270

Pro Ala Val Arg Pro Thr Pro Cys Ala Pro Leu Ala Glu Cys Lys Gly
            275                 280                 285

Leu Ser Leu Asp Glu Gly Pro Gly Lys Gly Thr Glu Glu Thr Ala Glu
290                 295                 300

Tyr Ser Ser Phe Lys Gly Gly Tyr Ala Lys Gly Leu Glu Gly Glu Ser
305                 310                 315                 320

Leu Gly Cys Ser Gly Ser Ser Glu Ala Gly Ser Ser Gly Thr Leu Glu
                325                 330                 335

Ile Pro Ser Ser Leu Ser Leu Tyr Lys Ser Gly Ala Val Asp Glu Ala
                340                 345                 350

Ala Ala Tyr Gln Asn Arg Asp Tyr Tyr Asn Phe Pro Leu Ala Leu Ser
            355                 360                 365

Gly Pro Pro His Pro Pro Pro Thr His Pro His Ala Arg Ile Lys
370                 375                 380

Leu Glu Asn Pro Ser Asp Tyr Gly Ser Ala Trp Ala Ala Ala Ala
385                 390                 395                 400

Gln Cys Arg Tyr Gly Asp Leu Ala Ser Leu His Gly Gly Ser Val Ala
            405                 410                 415

Gly Pro Ser Thr Gly Ser Pro Ala Thr Ala Ser Ser Ser Trp His
            420                 425                 430

Thr Leu Phe Thr Ala Glu Glu Gly Gln Leu Tyr Gly Pro Gly Gly Gly
            435                 440                 445

Gly Gly Ser Ser Ser Pro Ser Asp Ala Gly Pro Val Ala Pro Tyr Gly
    450                 455                 460

Tyr Thr Arg Pro Pro Gln Gly Leu Ala Ser Gln Glu Gly Asp Phe Ser
465                 470                 475                 480

Ala Ser Glu Val Trp Tyr Pro Gly Gly Val Val Asn Arg Val Pro Tyr
                485                 490                 495

Pro Ser Pro Ser Cys Val Lys Ser Glu Met Gly Pro Trp Met Glu Asn
            500                 505                 510

Tyr Ser Gly Pro Tyr Gly Asp Met Arg Leu Asp Ser Thr Arg Asp His
            515                 520                 525

Val Leu Pro Ile Asp Tyr Tyr Phe Pro Pro Gln Lys Thr Cys Leu Ile
            530                 535                 540

Cys Gly Asp Glu Ala Ser Gly Cys His Tyr Gly Ala Leu Thr Cys Gly
545                 550                 555                 560

Ser Cys Lys Val Phe Phe Lys Arg Ala Ala Glu Gly Lys Gln Lys Tyr
```

-continued

```
                565                 570                 575
Leu Cys Ala Ser Arg Asn Asp Cys Thr Ile Asp Lys Phe Arg Arg Lys
            580                 585                 590

Asn Cys Pro Ser Cys Arg Leu Arg Lys Cys Tyr Glu Ala Gly Met Thr
        595                 600                 605

Leu Gly Ala Arg Lys Leu Lys Lys Leu Gly Asn Leu Lys Leu Gln Glu
    610                 615                 620

Glu Gly Glu Asn Ser Ser Ala Gly Ser Pro Thr Glu Asp Pro Ser Gln
625                 630                 635                 640

Lys Met Thr Val Ser His Ile Glu Gly Tyr Glu Cys Gln Pro Ile Phe
                645                 650                 655

Leu Asn Val Leu Glu Ala Ile Glu Pro Gly Val Val Cys Ala Gly His
            660                 665                 670

Asp Asn Asn Gln Pro Asp Ser Phe Ala Ala Leu Leu Ser Ser Leu Asn
        675                 680                 685

Glu Leu Gly Glu Arg Gln Leu Val His Val Val Lys Trp Ala Lys Ala
    690                 695                 700

Leu Pro Gly Phe Arg Asn Leu His Val Asp Asp Gln Met Ala Val Ile
705                 710                 715                 720

Gln Tyr Ser Trp Met Gly Leu Met Val Phe Ala Met Gly Trp Arg Ser
                725                 730                 735

Phe Thr Asn Val Asn Ser Arg Met Leu Tyr Phe Ala Pro Asp Leu Val
            740                 745                 750

Phe Asn Glu Tyr Arg Met His Lys Ser Arg Met Tyr Ser Gln Cys Val
        755                 760                 765

Arg Met Arg His Leu Ser Gln Glu Phe Gly Trp Leu Gln Ile Thr Pro
    770                 775                 780

Gln Glu Phe Leu Cys Met Lys Ala Leu Leu Leu Phe Ser Ile Ile Pro
785                 790                 795                 800

Val Asp Gly Leu Lys Asn Gln Lys Phe Phe Asp Glu Leu Arg Met Asn
                805                 810                 815

Tyr Ile Lys Glu Leu Asp Arg Ile Ile Ala Cys Lys Arg Lys Asn Pro
            820                 825                 830

Thr Ser Cys Ser Arg Arg Phe Tyr Gln Leu Thr Lys Leu Leu Asp Ser
        835                 840                 845

Val Gln Pro Ile Ala Arg Glu Leu His Gln Phe Thr Phe Asp Leu Leu
    850                 855                 860

Ile Lys Ser His Met Val Ser Val Asp Phe Pro Glu Met Met Ala Glu
865                 870                 875                 880

Ile Ile Ser Val Gln Val Pro Lys Ile Leu Ser Gly Lys Val Lys Pro
                885                 890                 895

Ile Tyr Phe His Thr Gln
            900

<210> SEQ ID NO 22
<211> LENGTH: 12
<212> TYPE: DNA
<213> ORGANISM: Artificial sequence
<220> FEATURE:
<223> OTHER INFORMATION: Hypothetical oligonucleotide

<400> SEQUENCE: 22
gctggttgta ag                                                         12

<210> SEQ ID NO 23
```

```
<211> LENGTH: 4
<212> TYPE: PRT
<213> ORGANISM: Artificial sequence
<220> FEATURE:
<223> OTHER INFORMATION: Hypothetical peptide

<400> SEQUENCE: 23

Ala Gly Cys Lys
1

<210> SEQ ID NO 24
<211> LENGTH: 32
<212> TYPE: DNA
<213> ORGANISM: Artificial sequence
<220> FEATURE:
<223> OTHER INFORMATION: Synthetic oligonucleotide probe A

<400> SEQUENCE: 24
cttttgaaga agaccttaca gccctcacag gt                                        32

<210> SEQ ID NO 25
<211> LENGTH: 38
<212> TYPE: DNA
<213> ORGANISM: Artificial sequence
<220> FEATURE:
<223> OTHER INFORMATION: Synthetic oligonucleotide probe B

<400> SEQUENCE: 25
ggaccatgtt ttgcccattg actattactt tccacccc                                  38

<210> SEQ ID NO 26
<211> LENGTH: 15
<212> TYPE: PRT
<213> ORGANISM: Artificial sequence
<220> FEATURE:
<223> OTHER INFORMATION: Synthetic peptide

<400> SEQUENCE: 26

Asp His Val Leu Pro Ile Asp Tyr Tyr Phe Pro Pro Gln Lys Thr
1               5                   10                  15
```

DNA ENCODING ANDROGEN RECEPTOR FRAGMENT

RELATED APPLICATIONS

This is a continuation application of U.S. patent application Ser. No.: 09/497,822; filed Feb. 3, 2000 now U.S. Pat. No. 6,821,767, which is a divisional application of U.S. patent application Ser. No. 07/182,646; filed Apr. 15, 1988, now U.S. Pat. No.: 6,307,030, the disclosures of which are incorporated herein by reference in their entireties.

This invention was made in the course of research supported in part by grants from the National Institutes of Health (NIH HD 16910, HD 04466, and HD 18968).

TECHNICAL FIELD OF THE INVENTION

This invention relates to recombinant DNA molecules and their expression products. More specifically this invention relates to recombinant DNA molecules coding for androgen receptor protein, androgen receptor protein, and use of the DNA molecules and protein in investigatory, diagnostic and therapeutic applications.

BACKGROUND OF THE INVENTION

The naturally occurring androgenic hormones, testosterone and its 5α-reduced metabolite, dihydrotestosterone, are synthesized by the Leydig cells of the testes and circulate throughout the body where they diffuse into cells and bind to the androgen receptor protein ("AR"). Androgens, acting through their receptor, stimulate development of the male genitalia and accessory sex glands in the fetus, virilization and growth in the pubertal male, and maintenance of male virility and reproductive function in the adult. The androgen receptor, together with other steroid hormone receptors constitute a family of trans-acting transcriptional regulatory proteins that control gene transcription through interactions with specific gene sequences.

When prostate cancer is found to be confined to the prostate gland, the treatment of choice is surgical removal. However, 50 to 80% of prostate cancer patients already have metastases at the time of diagnosis. Most of their tumors (70 to 80%) respond to the removal of androgen by castration or by suppression of luteinizing hormone secretion by the pituitary gland using a gonadotropin releasing hormone analogue alone or in combination with an anti-androgen. The degree and duration of response to this treatment is highly variable (10% live<6 months, 50% live<3 years, and 10% live>10 years.) Initially cancer cells regress without androgen stimulation, but ultimately the growth of androgen independent tumor cells continues (35). At present it is not possible to predict on an individual basis which patient will respond to hormonal therapy and for how long. If poorly responsive patients could be identified early, they could be treated by alternative forms of therapy (e.g. chemotherapy) at an earlier stage when they might be more likely to respond.

Studies on androgen receptors in prostate cancer have suggested that a positive correlation may exist between the presence of androgen receptors in cancer cells and their dependence on androgenic hormone stimulation for growth. (An analogous situation exists in mammary carcinoma where there is a correlation between estrogen receptors and regression of the tumor in response to estrogen withdrawal). However, methodological problems in the measurement of androgen receptors have prevented the routine use of androgen receptor assays in the diagnostic evaluation of prostate cancer. Prior to our preparation of androgen receptor antibodies, all androgen receptor assays were based on the binding of [$^3$H]-labeled androgen. These assays have been unreliable in human prostate cancer tissue because of the extreme lability of the androgen binding site and the presence of unlabeled androgen in the tissue. Endogenous androgen occupies the binding site on the receptor and dissociates very slowly (t ½ 24–48 hr at 0C). A further problem is that biopsy samples are quite small, making it difficult to obtain sufficient tissue for [$^3$H$^-$]-androgen binding assays. Moreover, prostate cancer is heterogenous with respect to cell types. Thus within a single biopsy sample there is likely to be an uneven distribution of cells containing androgen receptors.

Development of the male phenotype and maturation of male reproductive function are dependent on the interaction of androgenic hormones with the androgen receptor protein and the subsequent function of the receptor as a trans-acting inducer of gene expression. It has become well established over the past twenty-five years that genetic defects of the androgen receptor result in a broad spectrum of developmental and functional abnormalities ranging from genetic males (46,XY) with female phenotype to phenotypically normal males with infertility. Isolation of the structural gene for the androgen receptor makes it possible to define the nature of these genomic defects in molecular terms. Analysis of the functional correlates of the genetic defects may lead to a better understanding of the regulation of androgen receptor gene expression and of the mechanism of androgen action in male sexual development and function.

The androgen insensitivity syndrome, known also as testicular feminization, is characterized by an inability to respond to androgen due to a defect in the androgen receptor, the protein that mediates the action of androgen within the cell. Androgen insensitivity is an inherited X-linked trait that occurs in both complete and incomplete forms. The complete form results in failure of male sex differentiation during embryogenesis and absence of virilization at puberty. The result is a 46,XY genetic male with testes and male internal ducts. The testes produce normal amounts of testosterone and Mullerian inhibiting substance. Consequently development of the uterus is inhibited as in the normal male. Because of the inability to respond to androgen, the external genitalia remain in the female phenotype with normal clitoris and labia. A small vagina develops from the urogenital sinus and ends in a blind pouch. At puberty feminization with breast development and female contours occur in response to testicular estrogen, however, there is no growth of sexual hair even though circulating testosterone concentrations are equal to or greater than levels in the normal male.

Incomplete forms of the androgen insensitivity syndrome include a spectrum of phenotypes resulting from varying degrees of incomplete androgen responsiveness. At one extreme, individuals have mild enlargement of the clitoris and sparse pubic hair. The opposite extreme is characterized by more complete masculinization with varying degrees of hypospadias deformity but predominantly a male phenotype. It has been reported that some adult men with severe oligospermia or azoospermia who are otherwise normal, have defects in the androgen receptor. These may include as many as 10% of infertile males.

The genetic defect eliciting this range of abnormalities is thought to be a single biochemical event at the level of the gene for the androgen receptor. The androgen receptor is a high affinity androgen binding protein that mediates the effects of testosterone and dihydrotestosterone by functioning as a trans-acting inducer of gene expression. For proper male sexual development to occur, there is a requirement for androgen and its receptor at a critical time during embryogenesis and during puberty. The majority of individuals with the androgen insensitivity syndrome have a history of affected family members, although about a third are thought to represent new mutations of this X-linked disorder. The incidence ranges from 1 in 20,000 to 60,000 male births.

In studies of families with clinical evidence of the androgen insensitivity syndrome, four main categories were recognized that range from the most severe, complete absence of receptor binding activity in a genetic male with female phenotype, to qualitatively normal receptor in affected individuals. Second in severity are affected individuals with qualitatively abnormal androgen binding by receptor present in normal levels. Examples include the failure of sodium molybdate (a reagent often used in studies on steroid receptors) to stabilize the receptor of affected individuals when molybdate is known to stabilize the wild-type receptor. Lability of the receptor under conditions that normally cause transformation has also been reported. A third group expresses a decreased amount of receptor with wild-type in vitro binding characteristics. The final grouping contains those androgen insensitivity patients in whom no abnormality in receptor is detected. In a recent study of this form of the syndrome, the androgen receptor was as capable of binding oligonucleotides as the wild-type receptor. Indeed, with the techniques available until only recently, it has been difficult in certain cases to document an androgen receptor defect in affected individuals.

Experimental methods used in assessing receptor defects in the past have relied on the ability of receptor to bind androgen with high affinity. The limitation of this methodology is that it is not possible to distinguish between the lack of expression of the receptor and loss of androgen binding activity. An example of how inadequate methodology complicates diagnosis is the absence of detectable receptor binding activity in patients who are partially virilized. It is theoretically possible for a mutation to occur which allows the receptor with defective androgen binding activity to induce gene transcription. Biologically active truncated forms of the glucocorticoid receptor that lack steroid binding activity but retain the DNA binding domain have been demonstrated using genetically engineered mutants.

Purification of the androgen receptor has been difficult to accomplish due to its low concentration and high degree of instability. Reported attempts at purification using either conventional methods of column chromatography or steroid-affinity chromatography have yielded insufficient amounts of receptor protein to allow even the preparation of monoclonal antibodies.

An early report on the partial purification of the androgen receptor was disclosed by Mainwaring et al. in "The use of DNA-cellulose chromatography and isoelectric focusing for the characterization and partial purification of steroid-receptor complexes," Biochem J, 134, 113–127 (1973). They used DNA-cellulose chromatography and isoelectric focusing to isolate the receptor from rat ventral prostate and determined its physiochemical properties. This group was among the first to attempt the use of steroid affinity chromatography in conjunction with conventional chromatography, using the affinity label 17B-bromoacetoxytestosterone in receptor purification (See Mainwaring et al., "Use of the affinity label 17B-bromoacetoxytestosterone in the purification of androgen receptor proteins," Perspectives in Steroid Receptor Research, (1980)). Partial purification of androgen receptor has also been attempted from other tissue sources, such as ram seminal vesicles (See Foekens et al., Molecular Cellular Endocr, 23, 173–186 (1981) and Foekens et al., "Purification of the androgen receptor of sheep seminal vesicles," Biochem Biophys Res Comm, 104, 1279–1286 (1982)). The partially purified receptor displayed characteristics of a proteolyzed receptor, but a purification of 2,000 fold was reported with a recovery of 33% (See Foekens et al., "Purification of the androgen receptor of sheep seminal vesicles," Biochem Biophys Res Comm, 104, 1279–1286 (1982)). Later attempts at purification continued to combine steroid affinity chromatography with conventional techniques, reportedly achieving significant purification, but recoveries too low for further analysis (See Chany et al., "Purification and characterization of androgen receptor from steer semenal vesicle," Biochemistry 21, 4102–4109 (1982), Chany et al., "Purification and characterization of the androgen receptor from rat ventral prostate," Biochemistry 22, 6170–6175 (1983) and Chang et al., "Affinity labeling of the androgen receptor in rat prostate cytosol with 17B-[(bromoacetyl)oxy]-5-alpha-androstan-3-one," Biochemistry 23, 2527–2533 (1984)). More recent studies examine the effectiveness of a variety of immobilized androgens for their ability to bind the androgen receptor (See De Larminat et al., "Synthesis and evaluation of immobilized androgens for affinity chromatography in the purification of nuclear androgen receptor," The Prostate 5, 123–140 (1984) and Bruchovsky et al, "Chemical demonstration of nuclear androgen receptor following affinity chromatography with immobilized ligands," The Prostate 10, 207–222 (1987)). Despite these efforts, the receptor has not been purified to homogeneity and the quantities of purified androgen receptor obtained have been insufficient for the production of antisera.

Clinical assays for the androgen receptor now include several methods. The most common is the binding of tritium-labeled hormone and measurement of binding using a charcoal adsorption assay. Either a natural androgen, such as dihydrotestosterone, or synthetic androgen, such as mibolerone or methyltrienolone (R1881), can be used. An advantage of the latter in human tissue is that it is not significantly metabolized and does not bind to the serum androgen binding protein, sex steroid binding globulin. A limitation of radioisotope labeling of receptor is interference caused by endogenous androgen. Although exchange assays for the androgen receptor have been described (See Carroll et al., J Steroid Biochem 21, 353–359 (1984) and Traish et al., J Steroid Biochem 23, 405–413 (1985)), their effectiveness is limited by the slow kinetics of dissociation of the endogenous receptor-bound androgen.

Another method used to assess receptor status is autoradiography. In this method disclosed in Barrack et al., "Current concepts and approaches to the study of prostate cancer," Progress in Clinical and Biological Research, 239, 155–187 (1987) the radioactively labeled androgen is incubated with slide-mounted tissue sections of small tissue biopsy specimens which are then frozen, sectioned and fixed. Nuclear localization of radioactivity is detected by exposure of tissue sections to x-ray film. This technique requires considerable technical expertise, is labor intensive, and requires extended periods of exposure time. It is therefore of limited usefulness in general clinical assays. Another problem is high levels of background signal, i.e. a high noise/signal ratio, making it difficult to distinguish receptor-bound nuclear radioactivity from unbound radioactivity distributed throughout the cells.

WO 87/05049(Shine) discloses a method for the production of purified steroid receptor proteins, specifically estrogen receptor proteins, through the expression of recombinant DNA encoding for such proteins in eukaryotic host cells. However, the reference does not disclose the sequence for androgen receptor protein, nor does it disclose a method for obtaining such a sequence.

SUMMARY OF THE INVENTION

The present invention provides a DNA sequence characterized by a structural gene coding for a polypeptide having substantially the same biological activity as androgen receptor protein. A DNA sequence encoding androgen receptor protein or a protein having substantially the same biological activity as androgen receptor activity is also provided. DNA sequences may be obtained from cDNA or genomic DNA, or prepared using DNA synthesis techniques.

The invention further discloses cloning vehicles comprising a DNA sequence comprising a structural gene encoding a polypeptide having substantially the same biological activity as androgen receptor protein. Cloning vehicles comprising a DNA sequence encoding androgen receptor protein or a protein having substantially the same biological activity as androgen receptor protein is also provided. The cloning vehicles further comprise a promoter sequence upstream of and operatively linked to the DNA sequence. In general the cloning vehicles will also contain a selectable marker, and, depending on the host cell used, may contain such elements as regulatory sequences, polyadenylation signals, enhancers and RNA splice sites.

The invention further provides cells transfected or transformed to produce androgen receptor protein or a protein having substantially the same biological activity as androgen receptor protein.

A further aspect of the invention provides a purified androgen receptor protein and purified polypeptides and proteins have substantially the same biological activity as androgen receptor protein, and methods for producing such proteins and polypeptides.

BRIEF DESCRIPTION OF THE DRAWINGS

FIG. 1 shows a comparison of DNA-binding domains of the human androgen receptor (hAR) with members of the nuclear receptor family. (A) is a comparison of oligo A nucleotide sequence (SEQ ID NO:1) with sequences of hAR (SEQ ID NO:2) and other nuclear receptors: hPR, human progesterone receptor (SEQ ID NO:3); hMR, human mineralocorticoid receptor (SEQ ID NO:4); hGR, human glucocorticoid receptor (SEQ ID NO:5); hER, human estrogen receptor (SEQ ID NO:6); hT3R, human thyroid hormone receptor (SEQ ID NO:7); hRAR, human retinoic acid receptor (SEQ ID NO:8). Chromosomal locations are shown in parentheses at the left. Nucleotide identity between oligo A and hAR is indicated with an asterisk. The percent homology with oligo A is in parentheses at the right of each sequence. (B) shows the structure of fibroblast clone ARHFL1 human fibroblast clone [1]. Nucleotide residues are numbered from the 5'-terminus. Restriction endonuclease sites were determined by mapping or were deduced from DNA sequence. The TGA translation termination codon, determined by comparison with hPR, hMR and hGR, follows a long open reading frame containing sequences homologous to those of other steroid receptors. Arrows indicate exon boundaries in genomic clone X05AR. The hatched area is the putative DNA-binding domain. (C) shows a comparison of amino acid sequences of the AR DNA-binding domain (SEQ ID NO:9) with sequences of the nuclear receptor family. AR amino acid sequence was deduced from nucleotide sequence of clone ARHFL1 and is numbered beginning with the first conserved cysteine residue (+). Amino acid numbers in parentheses at the left indicate the residue number of the first conserved cysteine from the references indicated below. Percent homology with hAR is indicated in parentheses on the right. The region of the DNA-binding domain from which the oligo A sequence was derived is underlined in hAR. Coding DNA of residues 1 to 31 is contained within genomic clone X05AR. Abbreviations are hPR, human progesterone receptor (SEQ ID NO:10); hMR, human mineralocorticoid receptor (SEQ ID NO:11); hGR, human glucocorticoid receptor (SEQ ID NO:12); hER, human estrogen receptor (SEQ ID NO:13); cVDR, chicken vitamin D receptor (SEQ ID NO:14); hT3R, human thyroid hormone receptor (SEQ ID NO:15); vERBA, erb A protein from avian erythroblastosis virus (SEQ ID NO:16); and hRAR, human retinoic acid receptor (SEQ ID NO:17). Abbreviations for amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

FIGS. 4A–I shows the double-stranded DNA sequence (SEQ ID NO:18) encoding the human androgen receptor protein.

FIGS. 5A–E shows the complete single-stranded DNA sequence (5082 bases) of the human androgen receptor (SEQ ID NO:18) and the deduced amino acid sequence (SEQ ID NO:19). No intron sequence is included.

FIGS. 6A–6D shows the complete single-stranded DNA sequence (4260 bases) of the rat androgen receptor (SEQ ID NO:20) and the deduced amino acid sequence (SEQ ID NO:21).

DETAILED DESCRIPTION OF THE INVENTION

Figure 2A:
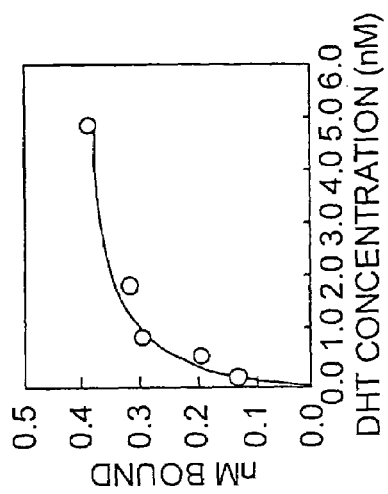
FIG. 2 illustrates the steroid binding properties of expressed AR cDNA. (A) shows the structure of pCMVAR in the expression vector pCMV containing the human cytomegalovirus (CMV) promoter of the immediate early gene, poly(A) addition-transcription terminator region of the human growth hormone gene (hGH poly A), SV40 origin of replication (SV40 Ori), and a polylinker region for insertion of cDNAs. The plasmid pTEBR contains the ampicillin resistance gene (Amp). (B) shows saturation analysis of [$^3$H]dihydrotestosterone binding in extracts of pCMVAR transfection of COS M6 cells. Portions of cytosol (0.1 ml, 0.3 mg/ml protein) were incubated overnight at 4° C. with increasing concentrations of $^3$H-labeled hormone and analyzed by charcoal adsorption. Nonspecific binding increased from 18% to 37% of total bound radioactivity. (C) shows a Scatchard plot analysis of [$^3$H]dihydrotestosterone binding. Error estimation was based on linear regression analysis (r=0.966). (D) illustrates the competition of unlabeled steroids for binding of 5 nM [$^3$H]dihydrotestosterone in transfected COS M6 cell extracts. Unlabeled steroids were added at 10- and 100-fold excess of labeled hormone. Specific binding was determined as previously described.

In the description the following terms are employed:

Nucleotide

A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U"). A and G are purines, abbreviated to R, and C, T, and U are pyrimidines, abbreviated to Y.

DNA Sequence

A linear series of nucleotides connected one to the other by phosphodiester bonds between the 3' and 5' carbons of adjacent pentoses.

Codon

A DNA sequence of three nucleotides (a triplet) which encodes through mRNA an amino acid, a translational start signal or a translational termination signal. For example, the nucleotide triplets TTA, TTG, CTT, CTC, CTA and CTG encode for the amino acid leucine ("Leu"), TAG, TAA and TGA are translational stop signals and ATG is a translational start signal.

Reading Frame

The grouping of codons during translation of mRNA into amino acid sequences. During translation the proper reading frame must be maintained. For example, the sequence GCTGGTTGTAAG (SEQ ID NO:22) may be translated in three reading frames or phases, each of which affords a different amino acid sequence:

GCT GGT TGT AAG-Ala-Gly-Cys-Lys (SEQ ID NO:23)
G CTG GTT GTA AG-Leu-Val-Val
GC TGG TTG TAA A-Trp-Leu-(Stop)

Polypeptide

A linear series of amino acids connected one to the other by peptide bonds between the a-amino and carboxy groups of adjacent amino acids.

Genome

The entire DNA of a substance. It includes inter alia the structural genes encoding for the polypeptides of the substance, as well as operator, promoter and ribosome binding and interaction sequences including sequences such as the Shine-Dalgarno sequences.

Structural Gene

A DNA sequence which encodes through its template or messenger RNA ("mRNA") a sequence of amino acids characteristic of a specific polypeptide.

Transcription

The process of producing mRNA from a structural gene.

Translation

The process of producing a polypeptide from mRNA.

Expression

The process undergone by a structural gene to produce a polypeptide. It is a combination of transcription and translation.

Plasmid

A non-chromosomal double-stranded DNA sequence comprising an intact "replicon" such that the plasmid is replicated in a host cell. When the plasmid is placed within a unicellular organism, the characteristics of that organism are changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage

Bacterial virus many of which include DNA sequences encapsidated in a protein envelope or coat ("capsid"). In a unicellular organism a phage may be introduced as free DNA by a process called transfection.

Cloning Vehicle

A plasmid, phage DNA or other DNA sequences which are able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning

The selection and propagation of a single species.

Recombinant DNA Molecule

A hybrid DNA sequence comprising at least two nucleotide sequences, the first sequence not normally being found together in nature with the second.

Expression Control Sequence

A DNA sequence of nucleotides that controls and regulates expression of structural genes when operatively linked to those genes.

To attain the objects of this invention it was necessary to determine the amino acid sequence and the DNA sequence of the structural gene encoding androgen receptor protein. One conventional approach would involve starting with the purified androgen receptor protein. However, as described above, significant amounts of the protein for such purposes have not been obtained.

An alternative approach to circumvent the overwhelming difficulty of androgen receptor protein purification is direct isolation of the DNA encoding the messenger RNA for androgen receptor protein.

Our strategy for isolating AR DNA was based on evidence that the AR gene is X-linked and that no other steroid receptor gene is located on the X chromosome. Sequence data are available from cDNAs for glucocorticoid, estrogen, progesterone, mineralocorticoid and vitamin D receptors. Comparison of the derived amino acid sequences has revealed a central region of high cysteine content which was found also in the v-erb A oncogene product recently identified as the thyroid hormone receptor. Within this 61–63 amino acid region is an arrangement of 9 cysteine residues that are absolutely conserved among steroid receptors thus far characterized. The overall homology among sequences in this conserved region ranges between 40 and 90%. We assumed that AR would resemble other members of the steroid receptor family in the conserved DNA-binding domain.

A human X chromosomal library was screened with the synthetic oligonucleotide probe A (Oligo A sequence=5'CTT TTG AAG AAG ACC TTA CAG CCC TCA CAG GT3'; SEQ ID NO:24) of FIG. 1(A) designed as a consensus sequence from the conserved sequence of the DNA-binding domain of other steroid receptors. Screening the library with the oligo A probe resulted in several recombinants whose inserts were cloned into bacteriophage M13 DNA and sequenced. One recombinant clone (Charon 35 X05AR) (human genomic clone [1]) contained a sequence similar to, yet distinct from, the DNA-binding domains of other steroid receptors. It had 84% sequence identity with oligo A, while other receptor DNAs were 78% to 91% homologous with consensus oligonucleotide.

From the nucleotide sequence just 5' of the DNA-binding domain, oligonucleotide probe B (Oligonucleotide B sequence=5'GGA CCA TGT TTT GCC CAT TGA CTA TTA CTT TCC ACC CC3'; SEQ ID NO:25) was synthesized and used to screen bacteriophage lambda gt11 cDNA libraries from human epididymis and cultured human foreskin fibroblasts. Recombinant phage (unamplified) screened with this oligonucleotide by in situ hybridization revealed one positive clone in each library. The epididymal clone (gt11 ARHEL1) (human epididymis clone [1]) contained the complete DNA-binding domain and approximately 1.5 kb of upstream sequence, whereas the fibroblast clone (gt11 ARHFL1) (human fibroblast clone [1]) shown in FIG. 1(B) contained the DNA-binding domain and 1.5 kb of downstream sequence. The DNA-binding domains of the cDNA isolates were identical to that of the genomic exon sequence.

Figure 2B:
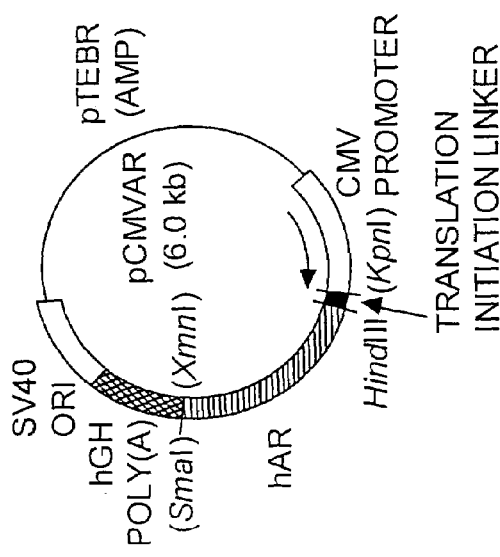
Figure 2D:
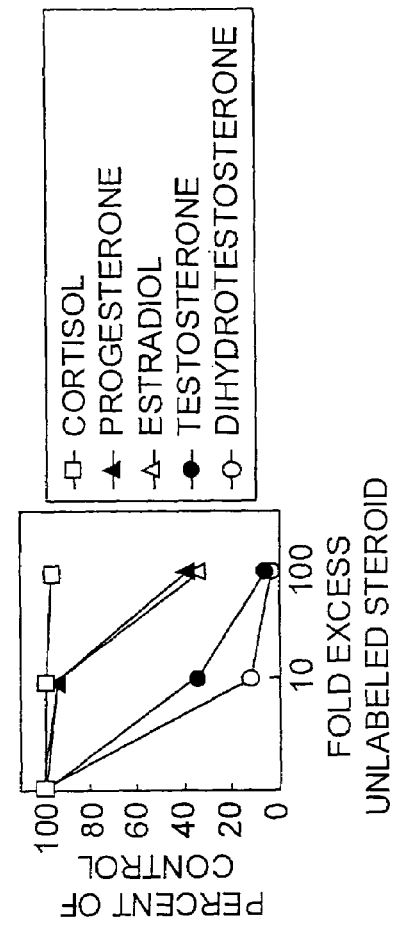
Figure 2C:
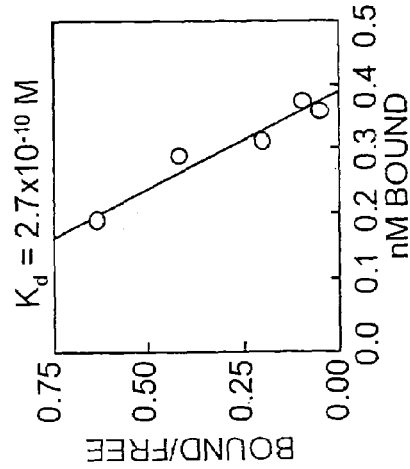

Transient expression in monkey kidney cells (COS M6) demonstrated that the human foreskin fibroblast cDNA fragment encodes the steroid-binding domain of hAR. A DNA fragment (ARHFLH-X) extending 5' to 3' from the Hind III site within the putative DNA-binding domain through the stop codon (TGA) was cloned into pCMV as shown in FIG. 2(A). Expression was facilitated by adding to the 5' end a consensus translation initiation sequence containing the methionine codon (ATG) in reading frame. Transfection of the recombinant construct produced a protein with high-affinity for [$^3$H]dihydrotestosterone, FIG. 2(C) saturable at physiological levels of hormone. See FIG. 2(B). The binding constant ($K_d$=2.7 (+1.4)$\times 10^{-10}$ M) was nearly identical to that of native AR. The level of expressed protein, 1.3 pmol per milligram of protein, was 20 to 60 times greater than that in male reproductive tissues. Mock transfections without plasmid or transfections with plasmid DNA lacking the AR insert yielded no specific binding of dihydrotestosterone. FIG. 2(D) shows steroid specificity was identical to that of native AR, with highest affinity for dihydrotestosterone and testosterone, intermediate affinity for progesterone and estradiol, and low affinity for cortisol.

Figure 3:
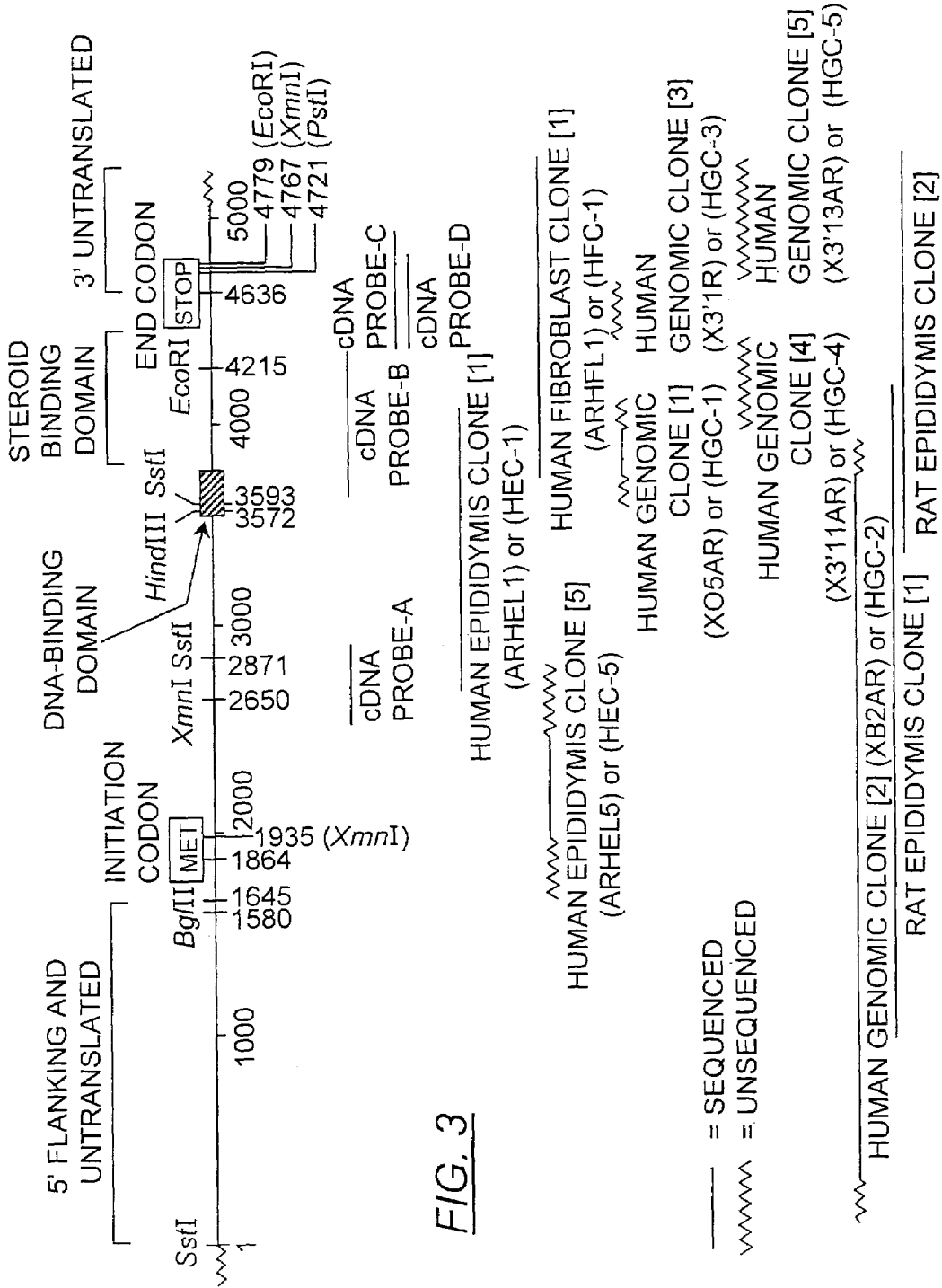
FIG. 3 is compiled clone map of the human androgen receptor. The map shows the structure of the human androgen receptor gene and the relative positions of the nucleic acid sequences contained in the cDNA probes [A], [B], [C] and [D], human fibroblast clone [1], human epididymis clones [1] and [5], human genomic clones [1], [2], [3], [4] and [5], and rat epididymis clones [1] and [2].

FIG. 3 is a clone map compiled to show the human androgen receptor gene and the nucleic acid sequences in the cDNA clones, human genomic clones, human fibroblast clones, human epididymis clones, and rat epididymis clones. Human fibroblast clone [1] extended through the stop codon or the C-terminal end of the androgen receptor protein. To isolate and elucidate the sequence of the 5' or N-terminal end of the androgen receptor protein, we used a EcoRl/Sstl fragment (EcoRl site was from the linker) from the 5' end of human epididymis clone [1] as a probe (cDNA probe [A]), to rescreen the human X chromosomal library by standard techniques. By these techniques, human genomic clone [2] was isolated and in turn used as a probe to rescreen a human epididymis library and isolate human epididymis clone [5]. The N-terminal sequence was elucidated along with the 5' flanking sequence of the androgen receptor protein and gene. Human genomic clones [3], [4] and [5] for the sequence 3' of human genomic clone [1] were obtained using cDNA probes B [a Hind III/EcoRl fragment] and C [an EcoRl fragment], by screening and isolating by standard techniques.

Two rat clones, rat epididymis clones [1] and [z], were isolated from a rat epididymis cDNA library using as probes the complete human epididymis clone [1] and a EcoRl/Pstl fragment, cDNA probe [D], respectively. These rat clones contained the entire protein coding sequence for the rat androgen receptor, plus flanking 5' and 3' untranslated sequences which were used to confirm the sequence of the human androgen receptor.

The complete double-stranded sequence (SEQ ID NO:18) encoding the human androgen receptor protein was determined and is set forth in FIG. 4. The single-stranded DNA sequence (SEQ ID NO:18) encoding human androgen receptor protein along with the amino acid sequence (SEQ ID NO:19) which it codes for are set forth in FIG. 5. The single stranded DNA sequence (SEQ ID NO:20) and the amino acid sequence (SEQ ID NO:21) for the rat androgen receptor protein is set forth in FIG. 6.

Recombinant DNA human fibroblast clone [1] isolated from human foreskin fibroblast cDNA gt11 expression library, human epididymis clones [1] and [5] isolated from human epididymis cDNA gt11 expression library were deposited in the American Type Culture Collection with accession numbers ATCC # 40439, ATCC # 40442 and ATCC # 40440, respectively. Human genomic clones [1], [2], [3], [4] and [5] which were isolated from human X chromosome lambda Charon 35 library available as ATCC # 57750 have been deposited with the American Type Culture Collection with accession numbers ATCC # 40441, ATCC # 40443, ATCC # 40444, ATCC # 40445 and ATCC # 40446, respectively.

A wide variety of host-cloning vehicle combinations may be usefully employed in cloning the double-stranded DNA disclosed herein. For example, useful cloning vehicles may include chromosomal, non-chromosomal and synthetic DNA sequences such as various known bacterial plasmids and wider host range plasmids such as pCMV and vectors derived from combinations of plasmids and phage DNA such as plasmids which have been modified to employ phage DNA expression control sequences. Useful hosts may include bacterial hosts, yeasts and other fungi, animal or plant hosts, such as Chinese Hamster Ovary Cells (CHO), or monkey kidney cells (COS M6), and other hosts. The particular selection of host-cloning vehicle combinations may be made by those of skill in the art after due consideration of factors such as the source of the DNA—i.e. genomic or cDNA.

Cloning vehicles for use in carrying out the present invention will further comprise a promoter operably linked to the DNA sequence encoding the androgen receptor protein. In some instances it is preferred that cloning vehicles further comprise an origin of replication as well as sequences which regulate and/or enhance expression levels, depending on the host cell selected.

Techniques for transforming hosts and expressing foreign cloned DNA in them are well known in the art (See, for example, Maniatis et al., infra). Cloning vehicles used for expressing foreign genes in bacterial hosts will generally contain a selectable marker, such as a gene for antibiotic resistance, and a promoter which functions in the host cell.

Eukaryotic microorganisms, such as the yeast *Saccharomyces cerevisiae*, may also be used as host cells. Cloning vehicles will generally comprise a selectable marker, such as the nutritional marker TRP, which allows selection in a host strain carrying a trpt mutation. To facilitate purification of an androgen receptor protein produced in a yeast transformant, a yeast gene encoding a secreted protein may be joined to the sequence encoding androgen receptor protein.

Higher eukaryotic cells can also serve as host cells in carrying out the present invention. Cultured mammalian cells are preferred. Cloning vehicles for use in mammalian cells will comprise a promoter capable of directing the transcription of a foreign gene introduced into a mammalian cell. Also contained in the expression vector is a polyadenylation signal, located downstream of the insertion site. The polyadenylation signal can be that of the cloned androgen receptor gene, or may be derived from a heterologous gene.

A selectable marker, such as a gene that confers a selectable phenotype, is generally introduced into the cells along with the gene of interest. Preferred selectable markers include genes that confer resistance to drugs, such as neomycin, hygromycin and methotrexate. Selectable markers may be introduced into the cell on a separate plasmid at the same time as the gene of interest, or they may be introduced on the same plasmid.

The copy marker of the integrated gene sequence can be increased through amplification by using certain selectable markers. Through selection, expression levels may be substantially increased.

Androgen receptor proteins may be purified from the host cells or cell media according to the present invention using techniques well known to those in the art. Such proteins may be utilized to produce monoclonal or polyclonal antibodies according to the techniques described below.

The techniques of this invention offer considerable advances over existing technology for measurement of androgen receptor. Utilizing proteins and peptides containing the disclosed sequences monoclonal or polyclonal antibodies can be produced for use as immunochemical reagents in immunodiagnostic assays. For example, radioimmunoassays and ELISA assays can be developed utilizing these reagents which will allow detection and quantification of androgen receptor in the presence of endogenous androgen since such androgen will not interfere with antibody binding to the receptor.

Immunocytochemistry utilizing our reagents enables determination and quantification of the cellular distribution of the androgen receptor in tumor tissues, which are often heterogenous in composition. This assay offers great potential for diagnostic evaluation of prostate cancer to determine to responsiveness to androgen withdrawal therapy.

In addition, the antibodies produced using the disclosed amino acid sequences can also be used in processes for the purification of androgen receptor protein produced by the above methods. One such purification process is disclosed in Logeat, F., et al., *Biochemistry* vol. 24 (1985), pp. 1029–1035, which is incorporated by reference herein.

Androgen receptor proteins and polypeptides synthesized from the deduced amino acid sequence can be used as immunogens for the preparation of antibodies to the androgen receptor. Peptides for such use range in length from about 3 to about 958 amino acids in length and are preferably from about 15 to about 30 amino acids in length. Shorter peptides may have significant sequence homology to other steroid receptor proteins and larger peptides may contain multiple antigenic determinants; these properties could result in antibodies with cross-reactivities to other steroid receptor proteins.

Peptides can be synthesized from amino acid sequences in the $NH_2$-terminal region, the DNA-binding domain, and the carboxyl-terminal steroid binding domain. Peptide selection will be based on hydropathic plots, selecting hydrophilic regions that are more likely exposed on the receptor surface. For diagnostic purposes preferred sequences will be selected from the $NH_2$-terminal region where there is the least homology with other steroid receptor proteins.

Peptides for use as immunogens can be synthesized using techniques available to one of ordinary skill in the art. For example, peptides corresponding to androgen receptor sequences can be synthesized using tBOC chemistry on a Biosearch Model 9500 peptide synthesizer. Peptide purity is assessed by high pressure liquid chromatography. Peptides can be conjugated to keyhole limpet hemocyanin through cysteine residues using the coupling agent m-maleimidobenzoyl-N-hydroxysuccinimide ester. One can also prepare resin-bound peptides utilizing the p-(oxymethyl benzamide) handle to attach the C-terminal amino acid to solid-phase resin support.

Proteins and peptides of this invention can be utilized for the production of polyclonal or monoclonal antibodies. Methods for production of such antibodies are known to those of ordinary skill in the art and may be performed without undue experimentation. One method for the production of monoclonal antibodies is described in Kohler, G., et al., "Continuous Culture of Fused Cells Secreting Antibody of Predefined Specificity," *Nature*, vol. 256 (1975), p. 495, which is incorporated herein by reference. Polyclonal antibodies, by way of example, can be produced by the method described below.

Peptide conjugates or resin-bound peptides can be injected into rabbits according to the procedure of Vaitukaitis et al., J Clin Endocrinol Metab, 33, 988–991 (1971) using a standard immunization schedule. Antisera titers can be determined in the ELISA assay.

For example, one androgen receptor sequence, $NH_2$-Asp-His-Val-Leu-Pro-Ile-Asp-Tyr-Tyr-Phe-Pro-Pro-Gln-Lys-Thr (SEQ ID NO:26) in the 5' region upstream from the DNA-binding domain, was used to raise antisera in rabbits. The antisera react selectively at a dilution of 1 to 500 with the androgen receptor both in its untransformed 8–10S form and in its 4–5S transformed form. Receptor sedimentation on sucrose gradients increases from 4 to 8–10S in the presence of antiserum at high ionic strength and from 8–10S to 11–12S at low ionic strength sucrose gradients. In the ELISA reaction against the peptide used as immunogen, reactivity was detectable at 1 to 25,000 dilution. This antiserum at a dilution of 1 to 3000 was found effective in staining nuclear androgen receptor in rat prostate and other male accessory sex glands (data not shown).

Our invention provides new molecular probes comprising complementary DNA sequences derived from the deduced sequences encoding the androgen receptor for diagnostic purposes. Such probes may be used to detect the presence of androgen receptor mRNA in tumor cells. Such probes may also be used for detection of androgen receptor gene defects. Androgen receptor complementary DNA sequences can be used as hybridization probes to detect abnormalities in the androgen receptor gene or in its messenger RNA.

Androgen receptor DNA sequences disclosed and complementary RNA sequences can be used to construct probes for use in DNA hybridization assays. An example of one such hybridization assay and methods for constructing probes for such assays are disclosed in U.S. Pat. No. 4,683,195 to Mullis et al., U.S. Pat. No. 4,683,202 to Mullis, U.S. Pat. No. 4,617,261 to Sheldon, III et al., U.S. Pat. No. 4,683,194 to Salki et al., and U.S. Pat. No. 4,705,886 to Levenson et al., which are hereby incorporated by reference.

By example, one method for detecting gene deletion utilizes Southern blotting and hybridization. DNA can be isolated from cultured skin fibroblasts or from leukocytes obtained from blood. DNA is cut with restriction enzymes, electrophoresed on an agarose gel, blotted onto nitrocellulose, and hybridized with [$^{32}$P]-labeled androgen receptor DNA (see Maniatis, T. et al., Molecular Cloning, A Laboratory Manual, Cold Spring Harbor Laboratory, 1982, incorporated by reference herein).

In addition, small mutations can be detected utilizing methods known to one of ordinary skill in the art, from cultured skin fibroblasts of the affected individual. A cDNA library can be prepared using standard techniques. The androgen receptor clones can be isolated using a [$^{32}$P]DNA AR probe. The AR cDNA clones can then be sequenced and compared to normal AR cDNA sequences.

Alternatively genomic DNA can be isolated from blood leukocytes or cultured skin fibroblasts of the affected individual. The DNA is then subjected to restriction enzyme digestion, electrophoresis and is blotted onto nitrocellulose. Synthetic oligonucleotides can be used to bracket specific exons. Exon sequences are amplified using the polymerase chain reaction, cloned into M13 and sequenced. The sequences are compared to normal human AR DNA sequences.

Another method of identifying small mutations or deletions takes advantage of the ability of RNase A to cleave regions of single stranded RNA in RNA:DNA hybrids, Genomic DNA isolated from fibroblasts of affected individuals is hybridized with radioactive RNA probes (Promego Biotec) prepared from wild-type androgen receptor cDNA. Mismatches due to mutations would be cleaved by RNase A and result in altered sized bands relative to wild-type on denaturing polyacrylamide gels.

Restriction fragment length polymorphism (RFLP) linked to the androgen receptor gene locus may be used in prenatal diagnosis and carrier detection of androgen insensitivity. For example, the presence of RFLPs in normal individuals is first established by isolating DNA from lymphocytes of at least six females (total of 12 X chromosomes). DNA can be isolated using the proteinase K procedure and fragmented using a battery of restriction enzymes. Preferred are those enzymes that contain the dinucleotide sequence CG in their recognition sequence. Southern blots are screened with 5–10 kb androgen receptor genomic fragments which if possible lack repetitive DNA. For those regions containing repetitive elements, total human genomic DNA can be added as competitor in the hybridization reaction. Alternatively, one can subclone selected regions to yield a probe free of repetitive elements.

Figure 8:
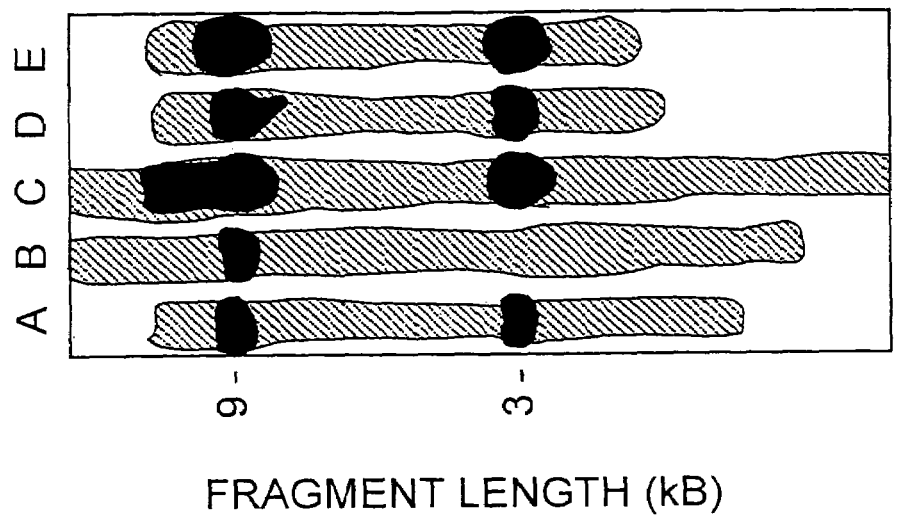
FIG. 8 is a photograph showing a Southern blot analysis in the human androgen receptor gene in complete androgen insensitivity syndrome patients.
Figure 7:
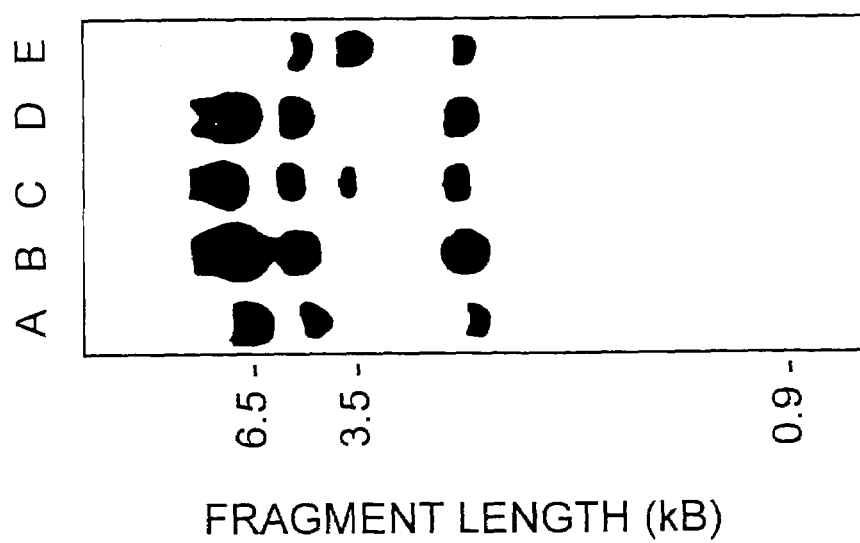
FIG. 7 is a photograph showing restriction fragment length polymorphisms in the human androgen receptor gene.

For example, a human restriction fragment length was determined by cDNA probe (B) and Hind III restriction endonuclease using the Southern blot technique (See FIG. 7). The two RFLP alleles detected are a fragment at 6.5 kb (allele 1) and a fragment at 3.5 kb (allele 2). Major constant fragment bands are seen at approximately 2 and 5 kb with minor constant bands at 0.9 and 7.5 kb. Allele 1 is present in approximately 30% of the X chromosomes of the Causasian population. Allele 2 is present in approximately 20% of the X chromosomes of the Causasian population. In FIG. 8 Lanes A, B and D, DNA from women who are homozygous for allele 1 is shown. In FIG. 8 Lane C, DNA from a woman who is heterozygous for both alleles 1 and 2 is shown. FIG. 8 Lane E contains DNA from a man that only possesses allele 2. This RFLP, and others determined by the clones we have isolated, will enable one to monitor the androgen receptor gene in various disease conditions described herein.

An example of using the androgen receptor clones to detect mutations is shown in FIG. 8 where five different complete androgen insensitive patients' DNA are digested with EcoRI, electrophoresed, Southern blotted, and probed with cDNA probe B. The patient in lane B lacks a 3 kb band indicating that part of the androgen receptor gene is deleted. Further analysis of this and other patients DNA is possible with other AR probes and by sequencing by standard methods and comparing the abnormal sequence to the normal sequence described herein.

Other potential uses for oligonucleotide sequences disclosed, for example in construction of therapeutics to block genetic expression, will be obvious to one of ordinary skill in the art.

What is claimed is:

1. An isolated and purified DNA fragment of the DNA sequence encoding SEQ ID NO:19 wherein said DNA fragment encodes a human androgen receptor fragment with androgen receptor activity.

2. A prokaryotic or eukaryotic host cell transformed or transfected with the DNA fragment of claim 1.

3. A viral or circular DNA plasmid comprising the DNA fragment of claim 1.

4. The viral or circular DNA plasmid according to claim 3 further comprising an expression control sequence operatively associated with said DNA fragment.

5. A prokaryotic or eukaryotic host cell transformed or transfected with the DNA fragment of claim 1.

6. A viral or circular DNA plasmid comprising the DNA fragment of claim 1.

7. The viral or circular DNA plasmid according to claim 6 further comprising an expression control sequence operatively associated with said DNA fragment.

* * * * *